(12) United States Patent
Benbow et al.

(10) Patent No.: US 8,071,606 B2
(45) Date of Patent: Dec. 6, 2011

(54) SUBSTITUTED PYRAZINONE AMIDES USEFUL FOR ACTIVATION OF GLUCOKINASE

(75) Inventors: John William Benbow, Norwich, CT (US); Jeffrey Allen Pfefferkorn, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 12/690,186

(22) Filed: Jan. 20, 2010

(65) Prior Publication Data

US 2010/0184777 A1 Jul. 22, 2010

Related U.S. Application Data

(60) Provisional application No. 61/262,600, filed on Nov. 19, 2009.

(51) Int. Cl.
*A61K 31/4965* (2006.01)
(52) U.S. Cl. .......... 514/255.06; 544/406; 546/268.1; 549/356
(58) Field of Classification Search ........... 514/255.06; 544/406; 546/268.1; 549/356
See application file for complete search history.

(56) References Cited

U.S. PATENT DOCUMENTS

| 2003/0139402 A1 | 7/2003 | Konradi et al. |
| 2004/0147512 A1 | 7/2004 | Konradi et al. |
| 2006/0058353 A1 | 3/2006 | Mckerrecher et al. ........ 514/337 |
| 2007/0213349 A1 | 9/2007 | Cheruvallath et al. ..... 514/266.3 |

FOREIGN PATENT DOCUMENTS

| EP | 1 433 778 | 6/2004 |
| JP | 2006-177436 | 7/2006 |
| WO | WO 93/04580 | 3/1993 |
| WO | WO 96/10016 | 4/1996 |
| WO | WO 97/28133 | 8/1997 |
| WO | WO 00/66557 | 11/2000 |
| WO | WO 02/20463 | 3/2002 |
| WO | WO 02/40448 | 5/2002 |
| WO | WO 02/051836 | 7/2002 |
| WO | WO 03/068230 | 8/2003 |
| WO | WO 03/092670 | 11/2003 |
| WO | WO 2004072066 | 8/2004 |
| WO | WO 2005/018557 | 3/2005 |
| WO | WO 2006/015159 | 2/2006 |
| WO | WO 2006/028833 | 3/2006 |
| WO | WO 2006/098683 | 9/2006 |
| WO | WO 2007/026761 | 3/2007 |
| WO | WO 2007043638 | 4/2007 |
| WO | WO 2007/058580 | 5/2007 |
| WO | WO 2007117995 | 10/2007 |
| WO | WO 2008079787 | 7/2008 |

OTHER PUBLICATIONS

Sarabu et al, Expert Opinion on Therapeutic Patents, vol. 18, No. 7, pp. 759-768, 2008.
R. Krause et al., Amino Acids, vol. 27, No. 1, pp. 9-18, 2004.
Moller, Nature 414, pp. 821-827, 2001.

*Primary Examiner* — James O Wilson
*Assistant Examiner* — Douglas M Willis
(74) *Attorney, Agent, or Firm* — John A. Wichtowski

(57) ABSTRACT

The present invention provides compounds of Formula (I)

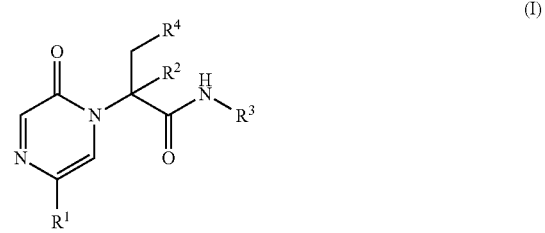

that act as glucokinase activators; pharmaceutical compositions thereof; and methods of treating diseases, disorders, or conditions mediated by glucokinase. The variables $R^1$, $R^2$, $R^3$ and $R^4$ are as described herein.

12 Claims, No Drawings

SUBSTITUTED PYRAZINONE AMIDES USEFUL FOR ACTIVATION OF GLUCOKINASE

CROSS REFERENCE TO RELATED APPLICATIONS

This application claims the benefit of U.S. Provisional Patent Application No. 61/262,600, filed on Nov. 19, 2009.

FIELD OF THE INVENTION

The present invention relates to substituted pyrazinone amide compounds, pharmaceutical compositions comprising the compounds and the uses thereof as glucokinase activators.

BACKGROUND

Diabetes is a major public health concern because of its increasing prevalence and associated health risks. The disease is characterized by metabolic defects in the production and utilization of carbohydrates which result in the failure to maintain appropriate blood glucose levels. Two major forms of diabetes are recognized. Type I diabetes, or insulin-dependent diabetes mellitus (IDDM), is the result of an absolute deficiency of insulin. Type II diabetes, or non-insulin dependent diabetes mellitus (NIDDM), often occurs with normal, or even elevated levels of insulin and appears to be the result of the inability of tissues and cells to respond appropriately to insulin. Aggressive control of NIDDM with medication is essential; otherwise it can progress into IDDM.

As blood glucose increases, it is transported into pancreatic beta cells via a glucose transporter. Intracellular mammalian glucokinase (GK) senses the rise in glucose and activates cellular glycolysis, i.e., the conversion of glucose to glucose-6-phosphate, and subsequent insulin release. Glucokinase is found principally in pancreatic β-cells and liver parenchymal cells. Because transfer of glucose from the blood into muscle and fatty tissue is insulin dependent, diabetics lack the ability to utilize glucose adequately which leads to undesired accumulation of blood glucose (hyperglycemia). Chronic hyperglycemia leads to decreases in insulin secretion and contributes to increased insulin resistance. Glucokinase also acts as a sensor in hepatic parenchymal cells which induces glycogen synthesis, thus preventing the release of glucose into the blood. The GK processes are, thus, critical for the maintenance of whole body glucose homeostasis.

It is expected that an agent that activates cellular GK will facilitate glucose-dependent secretion from pancreatic beta cells, correct postprandial hyperglycemia, increase hepatic glucose utilization and potentially inhibit hepatic glucose release. Consequently, a GK activator may provide therapeutic treatment for NIDDM and associated complications, inter alia, hyperglycemia, dyslipidemia, insulin resistance syndrome, hyperinsulinemia, hypertension, and obesity.

Several drugs each acting by different mechanisms are available for treating hyperglycemia and subsequently, NIDDM (Moller, D. E., "New drug targets for Type 2 diabetes and the metabolic syndrome" Nature 414; 821-827, (2001)). Insulin secretagogues, including sulphonyl-ureas (e.g., glipizide, glimepiride, glyburide) and meglitinides (e.g., nateglinide and repaglinide) enhance secretion of insulin by acting on the pancreatic beta-cells. While this therapy can decrease blood glucose level, it has limited efficacy and tolerability, causes weight gain and often induces hypoglycemia. Biguanides (e.g., metformin) are thought to act primarily by decreasing hepatic glucose production. Biguanides often cause gastrointestinal disturbances and lactic acidosis, further limiting their use. Inhibitors of alpha-glucosidase (e.g., acarbose) decrease intestinal glucose absorption. These agents often cause gastrointestinal disturbances. Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. Finally, insulin is used in more severe cases, either alone or in combination with the above agents.

Ideally, an effective new treatment for NIDDM would meet the following criteria: (a) it would not have significant side effects including induction of hypoglycemia; (b) it would not cause weight gain; (c) it would at least partially replace insulin by acting via mechanism(s) that are independent from the actions of insulin; (d) it would desirably be metabolically stable to allow less frequent usage; and (e) it would be usable in combination with tolerable amounts of any of the categories of drugs listed herein. Substituted heteroaryls, particularly pyridones, have been implicated in mediating GK and may play a significant role in the treatment of NIDDM. For example, U.S. Patent Publication No. 2006/0058353 and PCT publication Nos. WO2007/043638, WO2007/043638, and WO2007/117995 recite certain heterocyclic derivatives with utility for the treatment of diabetes. Although investigations are on-going, there still exists a need for a more effective and safe therapeutic treatment for diabetes, particularly NIDDM.

SUMMARY OF THE INVENTION

The present invention provides compounds of Formula (I) that are glucokinase mediators, in particular, glucokinase activators. As such, these compounds may be used in the treatment of diseases mediated by such activation (e.g., diseases related to Type 2 diabetes, and diabetes-related and obesity-related co-morbidities).

The compounds of the present invention are of Formula (I)

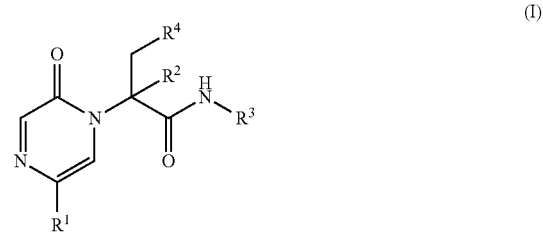

wherein $R^1$ is H, $(C_1-C_3)$alkyl, or halo-substituted $(C_1-C_3)$ alkyl; $R^2$ is H or $(C_1-C_3)$alkyl; $R^3$ is 5- or 6-membered heteroaryl containing one or two N heteroatoms, where said heteroaryl is optionally substituted with $R^{3a}$, where $R^{3a}$ is $(C_1-C_3)$alkyl, —$CF_3$, cyano, $(C_1-C_3)$alkoxy, halo, amino, $(C_1-C_3)$alkylamino-, di-$(C_1-C_3)$alkylamino-, —$C(O)OR^{3b}$, —$(C_1-C_3)$alkylC(O)OR^{3b}$, —$C(O)NR^{3b}R^{3b}$, or aryl$(C_1-C_3)$ alkyl-, where $R^{3b}$ and $R^{3a}$ are each independently H or $(C_1-C_3)$alkyl, and where the aryl of said aryl$(C_1-C_3)$alkyl is optionally substituted with $(C_1-C_3)$alkyl, —$CF_3$, cyano, $(C_1-C_3)$alkoxy, or halo;

R⁴ is (C₁-C₆)alkyl or

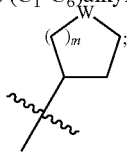

W is —CH₂ or O; and m is 0, 1 or 2; or a pharmaceutically acceptable salt thereof.

An embodiment of the present invention is the compound of Formula (I) wherein R¹ is H, methyl, ethyl, —CH₂F, —CHF₂, or —CF₃. Another embodiment of the present invention is the compound of Formula (I) wherein R¹ is methyl, —CHF₂, or —CF₃. Yet another embodiment of the present invention is the compound of Formula (I) wherein R¹ is —CF₃.

An embodiment of the present invention is the compound of Formula (I) wherein R² is H, methyl, or ethyl. Another embodiment of the present invention is the compound of Formula (I) wherein R² is H or methyl. Yet another embodiment of the present invention is the compound of Formula (I) wherein R² is H.

Another embodiment of the present invention is the compound of Formula (I) wherein R³ is pyrazolyl, pyridinyl, pyridazinyl, pyrimidinyl, or pyrazinyl, each optionally substituted with R³ᵃ, where R³ᵃ is (C₁-C₃)alkyl, —CF₃, cyano, (C₁-C₃)alkoxy, halo, amino, (C₁-C₃)alkylamino-, di-(C₁-C₃)alkylamino-, —C(O)OR³ᵇ, —C(O)NR³ᵇR³ᶜ, or aryl(C₁-C₃)alkyl-, where R³ᵇ and R³ᶜ are each independently H or (C₁-C₃)alkyl, and where the aryl of said arylalkyl is optionally substituted with (C₁-C₃)alkyl, —CF₃, cyano, (C₁-C₃)alkoxy, or halo. Yet another embodiment of the present invention is the compound of Formula (I) wherein R³ is pyrazolyl, pyridinyl, or pyrazinyl, each optionally substituted with R³ᵃ, where R³ᵃ is methyl, ethyl, cyano, methoxy, ethoxy, F, Cl, amino, —NHCH₃, —NHCH₂CH₃, —N(CH₃)₂, —CO₂H, —C(O)NHCH₃, —C(O)N(CH₃)₂, or benzyl, where said benzyl is optionally substituted with methyl, ethyl, methoxy, or ethoxy. A further embodiment of the present invention is where R³ is pyridinyl or pyrazinyl, or a group of Formula (a) or a group of Formula (b)

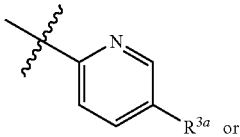 (a)

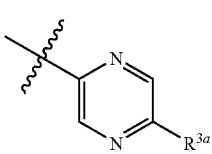 (b)

where R³ᵃ is methyl, —CH₂CO₂H or —CO₂H, and "⌇⌇⌇" is point of attachment. Further embodiments of the present invention are compounds of Formula (I) where W is —CH₂ and m is 1 and where W is O and m is 2.

Another embodiment of the present invention is a compound of Formula (1A)

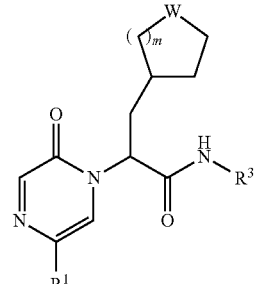 (1A)

where R¹, R³, W, and m are as described above.

Another embodiment of the present invention is a compound of Formula (1B)

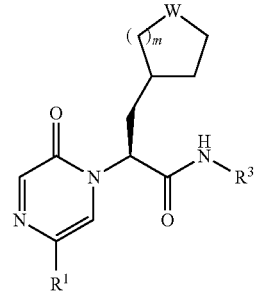 (1B)

where R¹, R³, W, and m are as described above.

Another embodiment of the present invention is a compound of Formula (1C)

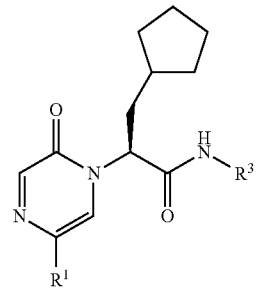 (1C)

where R¹ and R³ are as described above.

Specific embodiments of compounds of Formula (1C) are (S)-6-(3-cyclopentyl-2-(2-oxo-5-(trifluoromethyl)pyrazin-1(2H)-yl)propanamido)nicotinic acid; (S)-3-cyclopentyl-2-(2-oxo-5-(trifluoromethyl)pyrazin-1(2H)-yl)-N-(pyrazin-2-yl)propanamide; and (S)-3-cyclopentyl-N-(5-methylpyridin-2-yl)-2-(2-oxo-5-(trifluoromethyl)pyrazin-1(2H)-yl)propanamide.

Another embodiment of the present invention is a compound of Formula (1D)

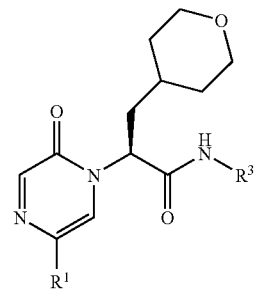 (1D)

where $R^1$ and $R^3$ are as described above. A specific embodiment of a compound of Formula (1D) is (S)-N-(5-methylpyridin-2-yl)-2-(2-oxo-5-(trifluoromethyl)pyrazin-1(2H)-yl)-3-(tetrahydro-2H-pyran-4-yl)propanamide.

Another embodiment of the present invention is a compound of Formula (1E)

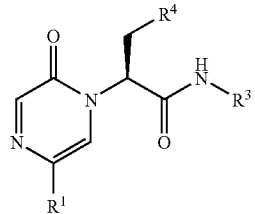

(1E)

where $R^1$, $R^3$ and $R^4$ are as described above. Another embodiment is the compound of Formula (1E) where $R^1$ is trifluoromethyl. Yet another embodiment is the compound of Formula (1E) where $R^3$ is pyridinyl or pyrazinyl, each optionally substituted with a methyl, $CO_2H$ or —$CH_2CO_2H$. A further embodiment is the compound of Formula (1E) where $R^4$ is isopropyl, cyclobutyl, cyclopentyl, cyclohexyl or tetrahydropyranyl. Still another embodiment is the compound of Formula (1E) where $R^1$ is trifluoromethyl; $R^3$ is pyridinyl or pyrazinyl, each optionally substituted with a methyl, —$CO_2H$ or —$CH_2CO_2H$ and $R^4$ is isopropyl, cyclobutyl, cyclopentyl, cyclohexyl or tetrahydropyranyl.

Another aspect of the present invention is a pharmaceutical composition that comprises: (a) a compound of the present invention, or a pharmaceutically acceptable salt thereof; and (b) a pharmaceutically acceptable excipient, diluent, or carrier. Preferably, the composition comprises a therapeutically effective amount of a compound of the present invention, or a pharmaceutically acceptable salt thereof, and a pharmaceutically acceptable excipient, diluent, or carrier.

The composition may comprise at least one additional pharmaceutical agent. Additional pharmaceutical agents include, for example, anti-diabetic, anti-obesity, anti-hypertension, anti-hyperglycemic, and lipid lowering agents, as described herein. More preferred, are anti-diabetic and anti-obesity agents, as described herein.

In yet another aspect of the present invention is a method for treating a disease, condition, or disorder mediated by glucokinase, in particular, activation of said enzyme, in a mammal that includes the step of administering to a mammal, preferably a human, in need of such treatment a therapeutically effective amount of a compound of the present invention, or a pharmaceutical composition thereof.

Diseases, disorders, or conditions mediated by glucokinase activators include Type II diabetes, hyperglycemia, metabolic syndrome, impaired glucose tolerance, glucosuria, cataracts, diabetic neuropathy, diabetic nephropathy, diabetic retinopathy, obesity, dyslididemia, hypertension, hyperinsulinemia, and insulin resistance syndrome. Preferred diseases, disorders, or conditions include Type II diabetes, hyperglycemia, impaired glucose tolerance, obesity, and insulin resistance syndrome. More preferred are Type II diabetes, hyperglycemia, and obesity. Most preferred is Type II diabetes.

In yet another aspect of the present invention is a method of reducing the level of blood glucose in a mammal, preferably a human, which includes the step of administering to a mammal in need of such treatment a therapeutically effective amount of a compound of the present invention, or a pharmaceutical composition thereof.

Compounds of the present invention may be administered in combination with other pharmaceutical agents (in particular, anti-obesity and anti-diabetic agents described herein). The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising: (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

DEFINITIONS

For purposes of the present invention, as described and claimed herein, the following terms and phrases are defined as follows:

"Activate(s)" or "activator", or "activation", as used herein, unless otherwise indicated, refers to the ability of the compounds of the present invention to indirectly or directly bind to the glucokinase enzyme in a mammal as a ligand thereby partially or wholly activating said enzyme.

"Alkoxy", as used herein, unless otherwise indicated, refers to an oxygen moiety having a further alkyl substituent. The alkyl portion (i.e., alkyl moiety) of an alkoxy group has the same definition as below. Non-exclusive examples of alkoxy include, methoxy, ethoxy, and the like.

"Alkyl", as used herein, unless otherwise indicated, includes saturated monovalent hydrocarbon alkane radicals of the general formula $C_nH_{2n+1}$. The alkane radical may be straight or branched and may be unsubstituted or substituted. For example, the term "($C_1$-$C_6$) alkyl" refers to a monovalent, straight or branched aliphatic group containing 1 to 6 carbon atoms. Non-exclusive examples of ($C_1$-$C_6$) alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. Alkyl represented along with another term (e.g., alkylamino- (e.g., $CH_3HN$—), aminoalkyl- (e.g., $NH_2CH_2$—), di-alkylamino- (e.g., $(CH_3)_2N$—), arylalkyl- (e.g., benzyl), and the like) where said alkyl moiety has the same meaning as above and may be attached to the chemical moiety by any one of the carbon atoms of the aliphatic chain.

"Aryl", as used herein, unless otherwise indicated, refers to a monocyclic aromatic ring. A typical aryl group (e.g., phenyl, napthyl) is a 6- to 10-membered carbocyclic ring or ring system. The aryl group may be attached to the chemical moiety by any one of the carbon atoms within the ring system. Aryl rings may be optionally substituted, typically with one to three substituents, preferably one substituent.

"Compound(s) of the present invention", as used herein, unless otherwise indicated, refers to compounds of Formulae (I), (1A), (1B), (1C), (1D) and (1E), pharmaceutically acceptable salts of the compounds, thereof, including all stereoisomers (e.g., enantiomers), tautomers and isotopically labeled compounds, and are, therefore, considered equivalents of the compounds of the present invention. Solvates and hydrates of the compounds of the present invention are considered compositions.

"Diabetes", as used herein, unless otherwise indicated, refers to metabolic defects in the production and utilization of carbohydrates, particularly glucose, which result in the failure of glucose homeostasis. Preferred forms of diabetes include Type I diabetes, or insulin-dependent diabetes mellitus (IDDM) which results from the absolute deficiency of insulin and Type II diabetes, or non-insulin dependent diabetes mellitus (NIDDM), which often occurs with normal, or even elevated levels of insulin and appears to be the result of the inability of mammalian cells and tissues to respond appropriately to insulin. Most preferred is NIDDM.

"Diabetes-related disorder", as used herein, unless otherwise indicated, refers to metabolic syndrome (also referred to as Syndrome X), hyperglycemia, hyper-insulinemia, impaired glucose tolerance, impaired fasting glucose, insulin resistance, obesity, atherosclerotic disease, cardiovascular disease, cerebrovascular disease, peripheral vessel disease, lupus, polycystic ovary syndrome, carcinogenesis, diabetic neuropathy, diabetic nephropathy, diabetic retinopathy, diabetic macular edema, and hyperplasia.

"Halo-substituted alkyl", unless otherwise indicated, refers to an alkyl group substituted with one or more halogen atoms (e.g., chloromethyl, dichloromethyl, fluoromethyl, difluoromethyl, trifluoromethyl, perfluoroethyl, and the like. When substituted, the alkane radicals are preferably substituted with 1 to 3 fluoro substituents.

"Heteroaryl", as used herein, unless otherwise indicated, refers to an aromatic monocyclic ring containing one or two nitrogen heteroatoms. Non-exclusive examples of monocyclic rings include pyrazolyl, pyridinyl, pyridazinyl, pyrimidinyl, and the like. The heteroaryl group may be attached to the chemical moiety by any one of the carbon atoms within the ring. Heteroaryls may be optionally substituted, typically with one to three substituents, preferably one substituent.

"Mammal", or "mammalian" as used herein, unless otherwise indicated, refers to an individual animal that is a member of the taxonomic class Mammalia. Non-exclusive examples of mammals include humans, dogs, cats, horses, and cattle, preferably human.

"Mediate(s)" or "mediated", as used herein, unless otherwise indicated, refers to the activation of the glucokinase enzyme by enhancing glucose binding, alleviating the inhibition of glucokinase regulatory protein, a key regulator of glucokinase activity in the liver, and/or to increase the catalytic rate of the glucokinase enzyme (e.g., change Vmax).

"Pharmaceutically acceptable" as used herein, unless otherwise indicated, indicates that the substance or composition must be compatible chemically and/or toxicologically, with the other ingredients comprising a formulation, composition, and/or the mammal being treated therewith.

"Reducing the level of blood glucose", or "lower blood glucose" as used herein, unless otherwise indicated, refers to an amount of the compound of the present invention sufficient to provide circulating concentrations of the compound high enough to accomplish the desired effect of lowering blood glucose levels in a mammal.

"Therapeutically effective amount", as used herein, unless otherwise indicated, refers to an amount of the compounds of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

"Treatment", "treating", and the like, as used herein, unless otherwise indicated, refers to reversing, alleviating, or inhibiting the progress of the disorder or condition to which such term applies, or one or more symptoms of such disorder or condition. As used herein, these terms also encompass, depending on the condition of the mammal, preferably a human, preventing the onset of a disorder or condition, or of symptoms associated with a disorder or condition, including reducing the severity of a disorder or condition or symptoms associated therewith prior to affliction with said disorder or condition. Thus, treatment can refer to administration of the compounds of the present invention to a mammal that is not at the time of administration afflicted with the disorder or condition. Treating also encompasses preventing the recurrence of a disorder or condition or of symptoms associated therewith.

DETAILED DESCRIPTION OF THE INVENTION

The present invention provides a compound of Formula (I), or a pharmaceutically acceptable salt thereof, and pharmaceutical compositions comprising these compounds that are useful in the treatment of diseases, disorders, or conditions mediated by glucokinase activation. In particular, the compounds and compositions of the invention are useful to activate glucokinase in a mammal, preferably a human.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art. See, for example, Louis F. Fieser and Mary Fieser, *Reagents for Organic Synthesis,* 1; 19, Wiley, New York (1967, 1999 ed.); or *Beilsteins Handbuch der organischen Chemie,* 4, Aufl. ed. Springer-Verlag, Berlin, including supplements (also available via the Beilstein online database)).

For illustrative purposes, the reaction schemes depicted below demonstrate potential routes for synthesizing key intermediates and compounds of the present invention. For a more detailed description of the individual reaction steps, see the Examples section below. Those skilled in the art will appreciate that other suitable starting materials, reagents, and synthetic routes may be used to synthesize the intermediates and compounds of the present invention and a variety of derivatives thereof. Further, many of the compounds prepared by the methods described below can be further modified in light of this disclosure using conventional chemistry well known to the skilled artisan.

Compounds of the present invention described herein contain at least one asymmetric or chiral center and, therefore, exist in different stereoisomeric forms. The R and S configurations are based upon the knowledge of known chiral inversion and retention chemistry. For example, the chirality of an intermediate undergoes an inversion when a nucleophile attacks from the opposite side of the leaving group, the product could be designated as R or S depending on the priorities of the groups attached to the stereocenter. See, e.g., *Stereochemistry of Organic Compounds*, by Ernest L. Eliel, Samuel H. Wilen, John Wiley and Sons, Inc. (1994). Whereas, if a nucleophile attaches to the same side as the leaving group, the chirality of intermediate is retained. In most of the examples, there is an inversion of the configuration where a compound with R configuration is converted to compound with an S configuration as the priorities of all four substituents at the stereocenter is retained. It is further noted that the intermediates can also be racemic (50:50 mixture of S and R), thereby producing racemic products. A chiral separation method can be used to separate these enantiomers to provide the specific isomers. It is further noted that the intermediates can also be racemic thereby producing racemic products. See, e.g., A Jean Jacques Andre Collet, Samuel H. Wilen, *Enantiomers, Racemates and Resolutions*, John Wiley and Sons, Inc. (1981) for a more detailed description of techniques that can be used to resolve stereoisomers of compounds from their racemic mixture. In addition, the present invention embraces all geometric and positional isomers. For example, if a compound of the present invention incorporates a double bond, both the cis- and trans-forms, as well as mixtures, are embraced within the scope of the invention.

In the preparation of compounds of the present invention, protection of remote functionality (e.g., primary or secondary amine) of intermediates from undesired reactions can be prepared using a protecting group. The term "protecting group" (Pg), refers to a substituent that is commonly employed to protect a particular functionality while reacting other functional groups on the compound. For example, an amine protecting group "$Pg^1$" or a carboxyl protecting group "$Pg^2$" is a substituent attached to an amine or carboxyl group that protects the amine or carboxyl functionality, respectively, of the compound. Suitable amine protecting groups include: 1-tert-butyloxycarbonyl (Boc), acyl groups including: formyl, acetyl, chloroacetyl, trichloro-acetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like; and acyloxy groups including: methoxycarbonyl, 9-fluorenylmethoxycarbonyl, 2,2,2-trifluoroethoxycarbonyl, 2-trimethylsilylethxoycarbonyl, vinyloxycarbonyl, allyloxycarbonyl, 1,1-dimethyl-propynyloxycarbonyl, benzyloxycarbonyl, p-nitrobenzyloxycarbony, 2,4-dichlorobenzyloxycarbonyl, and the like. Suitable carboxyl protecting groups include: alkyl-, benzyl-, substituted benzyl-, and silyl-esters. Representative carboxyl protecting groups include methyl-, ethyl-, and t-butyl-esters, trimethylsilyl-, t-butyldimethylsilyl-, diphenylmethyl-, benzhydryl-, cyanoethyl-, 2-(trimethylsilyl)ethyl-, nitroethyl-, 2-(trimethylsilyl)ethoxymethyl-esters, and the like. Suitable protecting groups and their respective uses are readily determined by the skilled artisan. See, e.g., T. W. Greene, *Protective Groups in Organic Synthesis*, John Wiley & Sons, New York, (1991) for a general description of protecting groups and their use.

The term "leaving group" or "L", as used herein, refers to the group with the meaning conventionally associated with it in synthetic organic chemistry, i.e., an atom or group displaceable under reaction (e.g., alkylating) conditions. Addition of the leaving group to the chemical moiety also refers to the activation of said moiety. Examples of leaving groups which undergo nucleophilic substitution include halo (e.g., Cl, F, Br, I), alkyl (e.g., methyl and ethyl), thiomethyl, triflates, tosylates, mesylates, and the like. The term "coupling reagent" refers to a chemical reagent that is commonly employed as an agent to couple or join two or more specific compounds to make a single combined compound. Suitable coupling agents include [O-(7-azabenzotriazol-1-yl)-N,N,N', N'-tetramethyluronium hexafluorophosphate], 1,1'-thiocarbonyldimidazole, and the like.

Reaction Scheme A-1 depicts the preparation of substituted pyrazinone amides of Formula (I). The compounds of Formula (I) are prepared via the coupling of an appropriately substituted 1-H-pyrazin-2-one of Formula (III) and an activated ester of Formula (IV) followed by subsequent acid catalyzed transamidation (Formula (II) to Formula (I)), or alternatively, ester hydrolysis of Formula (II) to the corresponding carboxylic acid of Formula (IIA) and coupling the carboxylic acid (IIA) with an appropriate amine, $H_2NR^3$, to afford the substituted pyrazinone amide of Formula (I).

Reaction Scheme A-1

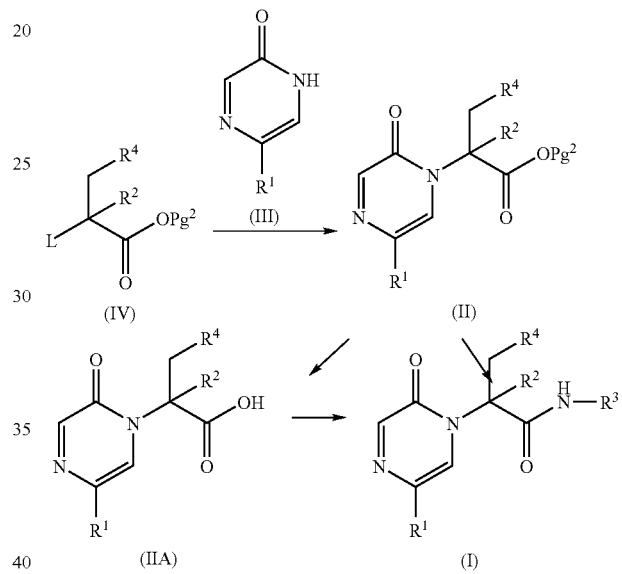

Reaction Scheme 1 further outlines the general procedures one can use to prepare compounds of the present invention. More particularly, Reaction Scheme 1 provides a depiction of the preparation of compounds of Formula (1A) which are compounds of Formula (I) in which $R^4$ is the ring which contains the variable W. It is to be understood that the compounds of Formula (I) in which $R^4$ is ($C_1$-$C_6$)alkyl can be prepared in an analogous fashion from analogous intermediates.

Reaction Scheme 1

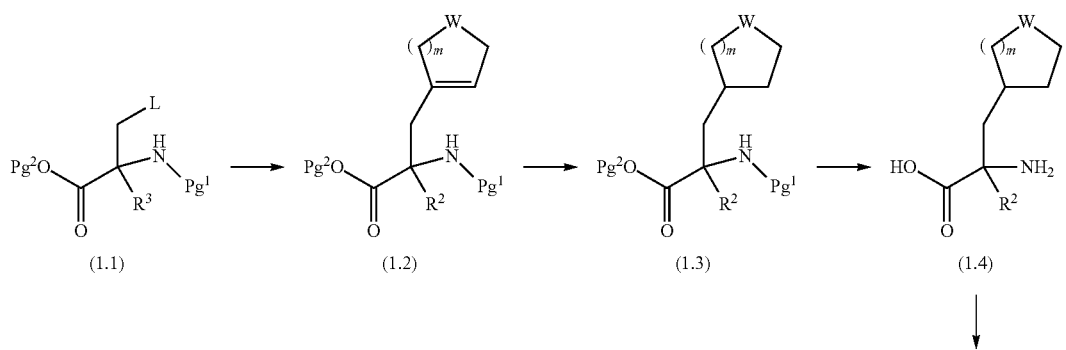

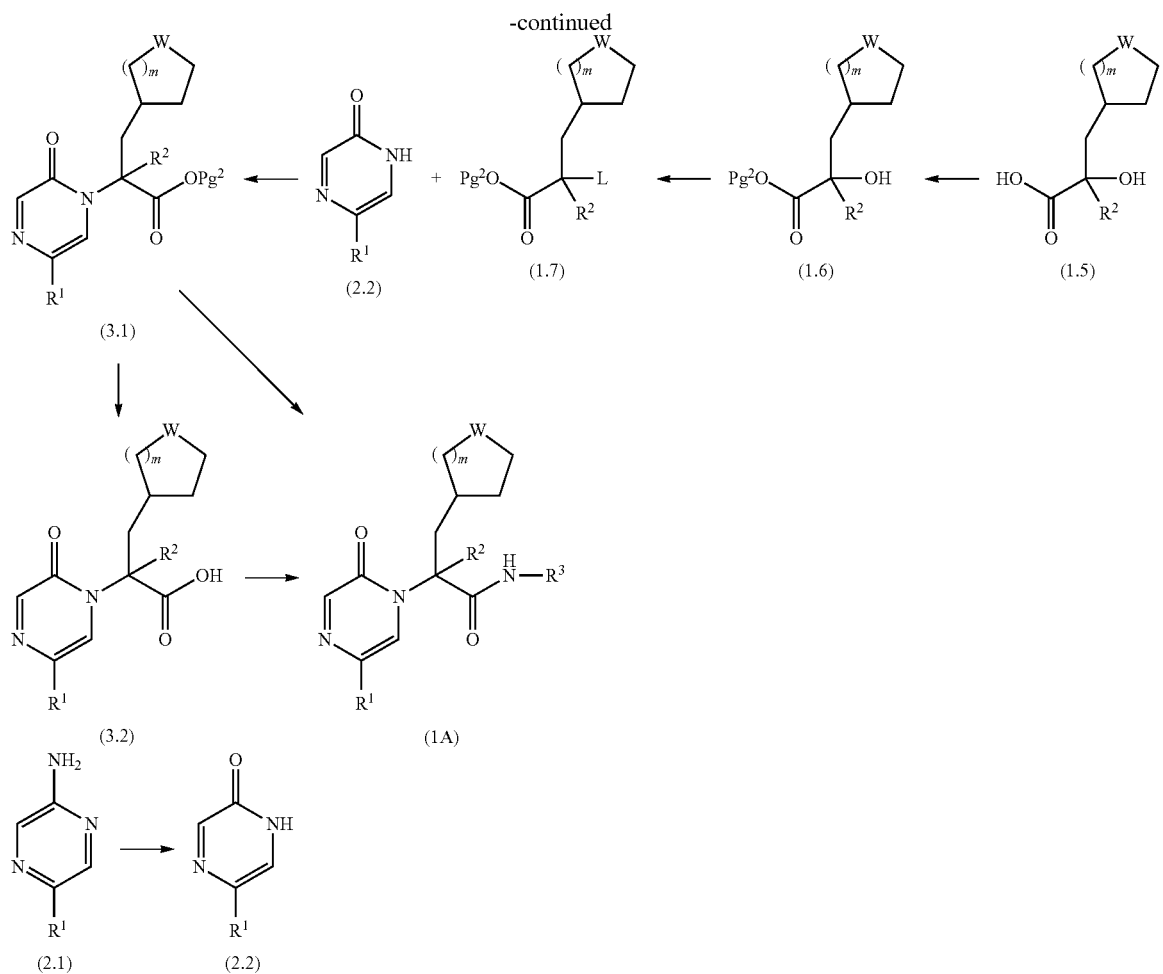

More particularly, Reaction Scheme 1 describes the preparation of substituted pyrazinone amides (1A) via the coupling of a 1-H-pyrazin-2-one (2.2) and an activated ester (1.7) followed by subsequent acid catalyzed transamidation (3.1 to 1A), or alternatively, ester hydrolysis of (3.1) to the corresponding carboxylic acid (3.2) and coupling the carboxylic acid with an appropriate amine to afford the substituted pyrazinone amide (1A).

The amino ester (1.2) can be synthesized from an appropriately functionalized amino-protected (N-Pg$^1$) and carboxyl-protected (O-Pg$^2$) derivative (1.1) with a leaving group (L, e.g., an iodo group) by metal (e.g., palladium) mediated coupling. See, e.g., Jackson, R. F. W., et. al., *Org. Syn.*, 81, 77, (2005). For example, 3,6-dihydro-2H-pyran-4-yl trifluoromethanesulfonate (available from J and W PharmLab, Levittown, Pa.) can be coupled with (R)-methyl 2-(tert-butoxycarbonylamino)-3-iodopropanoate (available from Amatek Chemical, Kowloon, Hong Kong) in the presence of PdCl$_2$(PPh$_3$)$_2$ after treating the former with zinc in an inert solvent such as dimethyl formamide. The olefin functionality in (1.2) can then be reduced to the corresponding saturated compound (1.3) under hydrogenation conditions. A typical hydrogenation reaction can be performed in methanol with hydrogen in the presence of a catalytic amount of Pd/C. Removal of the amino-protecting group, Pg$^1$, and the carboxyl-protecting group, Pg$^2$, of (1.3) provides the corresponding non-protected chiral α-amino acid (1.4). For example, the protecting groups can be cleaved under acidic condition, for example, HCl in water. The preparation of the chiral α-amino acid is not restricted to this method only. Alpha-amino acids can also be prepared by other methods known to the skilled artisan or can be purchased from commercial vendors (e.g., Sigma-Aldrich (St. Louis, Mo.); Acros Organics (Geel, Belgium); Fulcrum Scientific Limited (West Yorkshire, UK); and Amatek Chemical (Kowloon, Hong Kong)). The hydroxy-ester (1.5) can be prepared from the corresponding α-amino acid (1.4) by diazotization with sodium nitrite in water in the presence of an acid (e.g., sulfuric acid). See, e.g., McCubbin, J. A., et. al., *Org. Letters*, 8, 2993-2996, (2006). The α-hydroxy-ester (1.6) can be prepared from the corresponding hydroxy-ester (1.5) via acid catalyzed esterification, for example, in the presence of HCl. The activated ester (1.7) can be synthesized via treatment of the α-hydroxy-ester (1.6) with a leaving group such as trifluoromethanesulfonic anhydride. See, e.g., Degerbeck, F., et. al., *J. Chem. Soc., Perkin Trans.* 1, 11-14, (1993). In a typical procedure this reaction can be performed in an inert solvent such as anhydrous methylene chloride in the presence of a mild base such as 2,6-lutidine by dropwise addition of trifluoro-methanesulfonic anhydride to the α-hydroxy-ester (1.6).

The substituted pyrazinone (2.2) can be prepared from the corresponding amino pyrazine (2.1) (available from Sigma-Aldrich, St. Louis, Mo.; or Anichem LLC (Northbrunswick, N.J.) or can be prepared by common methods known to the skilled artisan (e.g., diazotization of the corresponding amino pyrazine with sodium nitrite in the presence of acidic water). For example, 5-(trifluoromethyl)pyrazin-2-amine can be treated with sodium nitrite and sulfuric acid in water to generate 5-(trifluoromethyl)-pyrazin-2(1H)-one. Intermediate (3.1) can then be prepared by a nucleophilic substitution reaction by treatment of a corresponding substituted pyrazinone (2.2) with lithium hexamethyldisilazide and subsequent addition of the activated (e.g., triflate) ester (1.7) thereby generating the corresponding pyrazinone ester (3.1). Other suitable bases with an appropriate $pK_b$ and other leaving group agents (e.g., alkyl sulfonates) can be used. See, for example, Effenberger, Franz et al. *Liebigs Annalen der Chemie*, (2), 314-33 (1986), and Terasaka, Tadashi et al. *Bioorganic & Medicinal Chemistry Letters*, 13(6), 1115-1118 (2003).

The final transformation to the compounds of the present invention can be accomplished via an acid catalyzed transamidation reaction of the pyrazinone ester (3.1). For example, transformation of the pyrazinone ester (3.1) to the pyrazinone amide (1A) can be achieved by treatment with a Lewis acid (e.g., $AlMe_3$, $AlMe_2Cl$, $Al_2O_3$, $TiO_2$, $ZnCl_2$, $SnCl_4$, $TiCl_4$, $FeCl_3$, $AlMe_3$, $AlMe_2Cl$, and the like) in the presence of an appropriate amine, $R^3NH_2$ (e.g., 3-aminopyrazole, aminopyrazine, or 2-amino-5-methyl pyridine (available from Sigma-Aldrich, St. Louis, Mo.). See, for example, Yadav, J. S., et. al., *Tet. Letters*, 48, Issue 24, 4169-4172, (1977).

Alternatively, this transformation can be achieved via ester hydrolysis of the pyrazinone ester (3.1) to the corresponding carboxylic acid (3.2) under acidic or basic conditions and coupling with an appropriate amine to prepare the pyrazinone amide, compounds of the present invention. Hydrolysis of the ester can be performed under either basic or acidic conditions. For base catalyzed hydrolysis, NaOH, KOH, or LiOH in the presence of an inert organic solvent such as THF or dioxane can be used. For acid catalyzed hydrolysis, HCl in the presence of water with or without an organic solvent can be used. See, e.g., Puschl, A., et. al., *J. Chem. Soc., Perkin Transactions*, 1, (21), 2757-2763, (2001). Other suitable methods known to the skilled artisan can be used to catalyze the hydrolysis. It is noted that the pyrazinone esters (3.1) can undergo a similar acid catalyzed transamidation reaction or ester hydrolysis for the amide transformation. Moreover, activation of the acid (3.2) to an acid chloride followed by treatment of the suitable amine will also afford compounds of the present invention.

Compounds of the present invention may be isolated and used per se or optionally administered in the form of its pharmaceutically acceptable salts, hydrates, and/or solvates. For example, it is well within the scope of the present invention to convert the compounds of the present invention into and use them in the form of their pharmaceutically acceptable salts derived from various organic and inorganic acids and bases, acids of amino acids, salts derived form organic and inorganic acids and cationic salts based on the alkali and alkaline earth metals in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydrofluoride, hydroiodide; other mineral acids and their corresponding salts such as sulfate, nitrate, phosphate; and alkyl and monoarylsulfonates such as ethanesulfonate, toluenesulfonate, and benzene sulfonate; and other organic acids and their corresponding salts such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include sulfate, pyrosulfate, bisulfate, sulfite, bisulfite, nitrate, phosphate, monohydrogenphosphate, dihydrogenphosphate, metaphosphate, pyrophosphate, trifluoroacetate, propionate, caprylate, isobutyrate, oxalate, malonate, succinate, suberate, sebacate, fumarate, acetate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like. Also contemplated are salts of amino acids such as arginate, gluconate, galacturonate, and the like. See, e.g., Berge S. M., et. al., Pharmaceutical Salts, *J. Pharm. Sci.*, 66:1 (1977).

Compounds of the present invention that comprise basic nitrogen-containing groups may be quaternized with such agents as $(C_1-C_4)$alkyl halides, e.g., methyl, ethyl, isopropyl, and tert-butyl chlorides, bromides, and iodides; di-$(C_1-C_4)$ alkyl sulfates, e.g., dimethyl-, diethyl-, and diamyl-sulfates; $(C_{10}-C_{18})$alkyl halides, e.g., decyl, dodecyl, lauryl, myristyl, and stearyl chlorides, bromides, and iodides; and aryl$(C_1-C_4)$ alkyl halides, e.g., benzylchloride and phenethyl bromide. Such salts permit the preparation of both water-soluble and oil-soluble compounds of the present invention.

When the compounds of the present invention possess a free acid form, a pharmaceutically acceptable base addition salt can be prepared by reacting the free acid form of the compound of the invention with a pharmaceutically acceptable organic or inorganic base. Non-exclusive examples of base addition salts include, but are not limited to alkali metal hydroxides including potassium, sodium, and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methyl-glutamine. Also included are aluminum salts of the compounds of the present invention. Further base salts of the present invention include, but are not limited to: copper, ferric, ferrous, lithium, magnesium, manganic, manganous, potassium, sodium, and zinc salts. Organic base salts include but are not limited to, salts of primary, secondary, and tertiary amines, substituted amines including naturally occurring substituted amines, cyclic amines, e.g., ammonium, tetramethylammonium, tetraethylammonium, methylamine, dimethylamine, trimethylamine, triethylamine, and ethylamine; and basic ion exchange resins, e.g., arginine, betaine, caffeine, chloroprocaine, choline, N,N'-dibenzylethylenediamine, dicyclohexylamine, diethanolamine, 2-diethylaminoethanol, 2-dimethylaminoethanol, ethanolamine, ethylenediamine, N-ethylmorpholine, N-ethylpiperidine, glucamine, and glucosamine. See, e.g., Berge, S. M., et. al., Pharmaceutical Salts, *J. Pharm. Sci.*, 66:1, (1977). It should be recognized that the free acid forms will typically differ from their respective salt forms somewhat in physical properties such as solubility in polar solvents, but otherwise the salts are equivalent to their respective free acid forms for the purposes of the present invention.

All of the salt forms are within the scope of the compounds of the present invention. Conventional concentration or crystallization techniques known by the skilled artisan can be employed to isolate the salts.

The compounds (and salts thereof) of the present invention may inherently form solvates, including hydrated forms, with pharmaceutically acceptable solvents. A solvate refers to a molecular complex of a compound of the present invention with one or more solvent molecules. Solvents that are commonly used in the pharmaceutical art, which are known to be innocuous to the recipient include water, ethanol, methanol, isopropanol, dimethylsulfoxide (DMSO), ethyl acetate, acetic acid, or ethanolamine, and the like. Although pharmaceutically acceptable solvents are preferred, other solvents may be used and then displaced with a pharmaceutically acceptable solvent to acquire certain polymorphs. A hydrate refers to the complex where the solvent molecule is water. Solvates, including hydrates, are considered compositions of the compound of the present invention.

It is also possible that the intermediates and compounds of the present invention may exist in different tautomeric forms. Tautomers refer to organic compounds that are interconvertible, i.e., when a chemical reaction results in a formal migration of a proton accompanied by a switch of a single bond and adjacent double bond (e.g., enol/keto, amide/imidic acid, and amine/imine forms) or as illustrated below

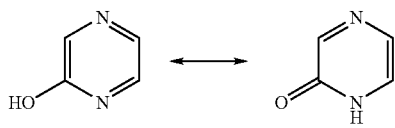

(e.g., Katritzky, A. R., et. al., *The Tautomerism of Heterocycles*, Academic Press, New York, (1976)). All such tautomeric forms are embraced within the scope of the present invention.

The present invention also includes isotopically-labelled compounds, which are identical to those recited for the compounds of the present invention, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively. Compounds of the present invention which contain the aforementioned isotopes and/or other isotopes of other atoms are within the scope of this invention.

Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Positron emitting isotopes such as $^{15}$O, $^{13}$N, $^{11}$C, and $^{18}$F are useful for positron emission tomography (PET) studies to examine substrate occupancy. Isotopically labeled compounds of this invention thereof can generally be prepared by carrying out the procedures disclosed herein, by substituting a readily available isotopically labelled reagent for a non-isotopically labeled reagent.

Compounds of the present invention are useful for treating diseases, conditions and/or disorders mediated by the activation of glucokinase. Another embodiment of the present invention is a pharmaceutical composition comprising a therapeutically effective amount of a compound of the present invention, or a pharmaceutically acceptable salt thereof, and a pharmaceutically acceptable excipient, diluent or carrier. The compounds of the present invention (including the compositions and processes used therein) may also be used in the manufacture of a medicament for the therapeutic applications described herein for use in medicine.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc., and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations can be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handled product.

The pharmaceutical composition (or formulation) may be packaged in a variety of ways depending upon the method used for administering the drug. Generally, an article for distribution includes a container having deposited therein the pharmaceutical formulation in an appropriate form. Suitable containers are well-known to the skilled artisan and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders mediated by the activation of glucokinase in a mammal that includes administering to a mammal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the activation of glucokinase which include: eating disorders (e.g., binge eating disorder, anorexia, bulimia, weight loss or control and obesity), prevention of obesity and insulin resistance by glucokinase expression in skeletal muscle of transgenic mice (Otaegui, P. J., et. al., *The FASEB Journal*, 17; 2097-2099, (2003)); and Type II diabetes, insulin resistance syndrome, insulin resistance, and hyperglycemia (Poitout, V., et. al., "An integrated view of β-cell dysfunction in type-II diabetes", *Annul. Rev. Medicine,* 47; 69-83, (1996)).

One aspect of the present invention is the treatment of Type II diabetes, progression of disease in Type II diabetes, metabolic syndrome (Syndrome X), obesity, hyperglycemia, impaired glucose tolerance (a pre-diabetic state of dysglycemia associated with insulin resistance), glucosuria (abnormal condition of osmotic diuresis due to excretion of glucose by the kidneys), cataracts, diabetic neuropathy, diabetic nephropathy, diabetic retinopathy, and conditions exacerbated by obesity (e.g., hypertension; dyslipidemia; hyperinsulinemia). The preferred disease, disorder, or condition to be treated is Type II diabetes, hyperglycemia, and obesity. Most preferred is Type II diabetes and hyperglycemia.

Diabetes is generally defined as a syndrome characterized by disordered metabolism and inappropriately high blood glucose (hyperglycemia) resulting from either low levels of the hormone insulin or from abnormal resistance to insulin's effects coupled with inadequate levels of insulin secretion to compensate. Diabetes is generally characterized as three main forms: (1) Type I, (2) Type II, and (3) gestational diabetes. Type I diabetes is usually due to autoimmune destruction of the pancreatic beta cells. Type II diabetes is characterized by insulin resistance in target tissues. This causes a need for abnormally high amounts of insulin and diabetes develops when the beta cells cannot meet this demand. Gestational diabetes is similar to Type II diabetes in that it involves insulin resistance; the hormones of pregnancy can cause insulin resistance in women genetically predisposed to developing this condition, and typically resolves with delivery of the child. However, Types I and II are chronic conditions. Type 1 diabetes, in which insulin is not secreted by the pancreas, is directly treatable with insulin, although dietary and other lifestyle adjustments are part of disease management. Type II diabetes may be managed with a combination of diet and pharmaceutical products (e.g., medicaments) and, frequently, insulin supplementation. Diabetes can cause many complications. Acute complications include hypoglycemia, hyperglycemia, ketoacidosis or nonketotic hyperosmolar coma. Serious long-term complications include, but are not limited to: cardiovascular disease, renal failure, retinal damage, decreased blood circulation, nerve damage, and hypertension.

In yet another aspect of the present invention is the treatment of diabetes related disorders, such as metabolic syndrome. Metabolic syndrome includes diseases, a combination of conditions or disorders such as dyslipidemia, hypertension, insulin resistance, coronary artery disease, obesity, and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology,* 7(2), (2005); and Alberti, K. G., et al., "The Metabolic Syndrome—A New Worldwide Definition," *Lancet,* 366, 1059-62 (2005). Preferably, administration of the compounds of the present invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant ($p<0.05$) reduction in glucose serum levels.

For a normal adult human having a body weight of about 100 kg, a dosage in the range of from about 0.001 mg to about 10 mg per kilogram body weight is typically sufficient, preferably from about 0.01 mg/kg to about 5.0 mg/kg, more preferably from about 0.01 mg/kg to about 1 mg/kg. However, some variability in the general dosage range may be required depending upon the age, weight, and general health of the subject being treated, the intended route of administration, the particular compound being administered, and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders as described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable anti-obesity agents include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $β_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-γ antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818, 658), lipase inhibitor (e.g., Cetilistat), $PYY_{3-36}$ (as used herein "$PYY_{3-36}$" includes analogs, such as pegylated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine. Preferably, compounds of the present invention and combination therapies are administered in conjunction with exercise and a sensible diet.

Suitable anti-diabetic agents include an acetyl-CoA carboxylase-2 (ACC-2) inhibitor, a phosphodiesterase (PDE)-10 inhibitor, a diacylglycerol acyltransferase (DGAT) 1 or 2 inhibitor, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) agonist (e.g., exendin-3 and exendin-4), a protein tyrosine phosphatase-1B (PTP-1B) inhibitor (e.g., trodusquemine, hyrtiosal extract, and compounds disclosed by Zhang, S., et al., *Drug Discovery Today*, 12 (9/10), 373-381 (2007)), SIRT-1 inhibitor (e.g., reservatrol), a dipeptidyl peptidase IV (DPP-IV) inhibitor (e.g., sitagliptin, vildagliptin, alogliptin and saxagliptin), an insulin secretagogue, a fatty acid oxidation inhibitor, an A2 antagonist, a c-jun amino-terminal kinase (JNK) inhibitor, insulin, an insulin mimetic, a glycogen phosphorylase inhibitor, a VPAC2 receptor agonist and a glucokinase activator. Preferred anti-diabetic agents are metformin and DPP-IV inhibitors (e.g., sitagliptin, vildagliptin, alogliptin and saxagliptin).

Suitable antihyperglycemic agents include, but are not limited to, alpha-glucosidase inhibitors (i.e., acarbose), biguanides, insulin, insulin secretagogues (i.e., sulfonureas (i.e., gliclazide, glimepiride, glyburide) and nonsulfonylureas (i.e., nateglinide and repaglinide)), thiazolidinediones (i.e. pioglitazone, rosiglitazone), and the like.

Suitable lipid lowering agents include, but are not limited to, HMGCoA reductase inhibitors, fibrates, microsomal triglyceride transfer protein inhibitors, cholesterol transfer protein inhibitors, acyl transfer protein inhibitors, low density lipid antioxidants, and the like.

Suitable antihypertensive agents include, but are not limited to, diuretics, adrenergic beta-antagonists, adrenergic alpha-antagonists, angiotensin-converting enzyme inhibitors, calcium channel blockers, ganglionic blockers, vasodilators, and the like.

According to the methods of the invention, when a compound of the present invention and at least one other pharmaceutical agent are administered together, such administration can be sequential in time or simultaneous with the simultaneous method being generally preferred. For sequential administration, a compound of the present invention and the additional pharmaceutical agent can be administered in any order. It is generally preferred that such administration be oral. It is especially preferred that such administration be oral and simultaneous. When a compound of the present invention and the additional pharmaceutical agent are administered sequentially, the administration of each can be by the same or by different methods, for example, tablet and syrup or capsule and parenteral injection or infusion. Administration and dosing will be determined by the prescribing practitioner.

The starting materials and reagents used in preparing these compounds are either available from commercial suppliers, e.g., Sigma-Aldrich (St. Louis, Mo.), Acros Organics (Geel, Belgium), J and W PharmLab (Levittown, Pa.), Amatek Chemical (Kowloon, Hong Kong), Fulcrum Scientific Limited (West Yorkshire, UK), and Anichem LLC (Northbrunswick, N.J.) or may be prepared by methods well known to the skilled artisan, following procedures described in such standard references as Fieser and Fieser's *Reagents for Organic Synthesis*, Vols. 1-17, John Wiley and Sons, New York, N.Y., (1991); *Rodd's Chemistry of Carbon compounds*, Vols. 1-5 and supps., Elsevier Science Publishers, (1989); *Organic Reactions*, Vols. 1-40, John Wiley and Sons, New York, N.Y., (1991); March J., *Advanced Organic Chemistry*, 4th ed., John Wiley and Sons, New York, N.Y.; and Larock, *Comprehensive Organic Transformations*, VCH Publishers, New York, (1989). Anhydrous tetrahydrofuran (THF), methylene chloride ($CH_2Cl_2$), and N,N-dimethylformamide may be purchased from Aldrich in Sure-Seal bottles and used as received. Solvents may be purified using standard methods known to those skilled in the art, unless otherwise indicated. Further, starting materials were obtained from commercial suppliers and used without further purification, unless otherwise indicated.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 precoated plates (Merck Art 5719) and eluted with appropriate solvent ratios (v/v). Reactions were assayed by TLC or LCMS and terminated as judged by the consumption of starting material. Visualization of the TLC plates was done with UV light (254 nM wavelength) or with an appropriate TLC visualizing solvent and activated with heat. Flash column chromatography (Still et al., *J. Org. Chem.* 43, 2923, (1978)) was performed using silica gel 60 (Merck Art 9385) or various MPLC systems, such as Biotage or ISCO purification system.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography (TLC)), recrystallization, and differential (i.e., liquid-liquid) extraction techniques. Biotage materials were purchased from Biotage AB (Charlottesville, Va.).

The compound structures in the examples below were confirmed by one or more of the following methods: proton magnetic resonance spectroscopy, mass spectroscopy, and elemental microanalysis. Proton magnetic resonance ($^1$H NMR) spectra were determined using a Bruker or Varian spectrometer operating at a field strength of 300 or 400 megahertz (MHz). Chemical shifts are reported in parts per million (PPM, δ) downfield from an internal tetramethylsilane standard. Alternatively, $^1$H NMR spectra were referenced to signals from residual protons in deuterated solvents as follows: $CDCl_3$=7.25 ppm; DMSO-$d_6$=2.49 ppm; $C_6D_6$=7.16 ppm; $CD_3OD$=3.30 ppm. Mass spectra (MS) data were obtained using Agilent mass spectrometer or Waters Micromass spectrometer with atmospheric pressure chemical or electron spray ionization. Method: Acquity UPLC with chromatography performed on a Waters BEH C18 column (2.1×30 mm, 1.75 µm) at 60° C. The mobile phase was a binary gradient of acetonitrile (containing 0.05% trifluoroacetic acid) and water (5-95%) Elemental microanalyses were performed by Atlantic Microlab Inc. and gave results for the elements stated within ±0.4% of the theoretical values.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

All of the recited U.S. patents and publications, including technical bulletins, references, documents foreign patents and applications and books are incorporated herein by reference in their entireties.

EXAMPLES

Preparation of Key Intermediates and Starting Materials

The following reactants provide a more detailed description of the process conditions. It is to be understood, however, that the invention, as fully described herein and as recited in the claims, is not intended to be limited by the details of the following schemes or modes of preparation. In the following intermediates, Boc refers to 1-tert-butyloxycarbonyl, and Tf refers to triflate.

Intermediate (1a): 3,6-dihydro-2H-pyran-4-yl trifluoromethanesulfonate

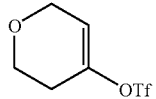
(1a)

Under argon, diisopropylamine (66.8 g, 92.5 mL), 0.66 mol) was dissolved in THF (1 L) and cooled to −5° C. in an ice/methanol bath. Over 30 minutes, n-butyllithium (2.34M, 290 mL, 0.66 mol) was added while maintaining the temperature below 1° C. The mixture was stirred at about 0° C. to about −5° C. for 15 minutes and cooled to −72° C. with an acetone and dry ice bath. Dihydro-2H-pyran-4(3H)-one was added slowly over 15 minutes while maintaining the temperature at −78° C. for 1 hour. N-phenyl-bis-(trifluoromethyl sulfonamide) was suspended in THF (500 mL) and added slowly to the mixture while maintaining a temperature below −60° C. The mixture was left stirring in the cooling bath, warming to room temperature overnight. The mixture was concentrated under reduced pressure. The residue were slurried in hexane at 50° C. (1 L and 250 mL), the liquors were concentrated under reduced pressure to afford Intermediate (1a). $^1$H NMR (CDCl$_3$, 300 MHz) δ 5.74 (1H), 4.19 (2H), 3.80 (2H), 2.39 (2H).

Intermediate (1b): (R)-methyl 2-(tert-butoxycarbonyl)-3-(3,6-dihydro-2H-pyran-4-yl)propanoate

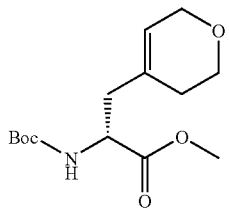
(1b)

In rigorously anaerobic conditions, zinc dust (72.7 g, 1.11 mol) was suspended in anhydrous N,N-dimethylformamide (100 mL), and to the stirred solution, trimethylsilyl chloride (23 mL 0.18 mol) was added (exotherm to 55° C.). The mixture was stirred for 20 minutes, during which time the supernatant became brown in color. The mixture was allowed to settle, and the supernatant decanted off using vacuum. The activated zinc powder was washed with N,N-dimethylformamide (4×50 mL), until the supernatant solvent became colorless.

(R)-methyl 2-(tert-butoxycarbonylamino)-3-iodopropanoate (85 g, 0.26 mol) (Sigma-Aldrich, Milwaukee, Wis.) was dissolved in N,N-dimethylformamide under argon, added in one portion to the activated zinc powder and stirred briskly. After approximately 5 minutes, the mixture self heated rapidly (21-30° C. over about 15 seconds). The stirring was stopped and the cooling bath immediately applied, allowing the exothermic reaction to be ceased at 50° C. As the temperature subsided, the cooling bath was removed and the mixture stirred at ambient temperature for 20 minutes and allowed to settle. The supernatant was syringed into a pre-prepared solution of Intermediate (1a) (60 g, 0.26 mol) and PdCl$_2$(PPh$_3$)$_2$ (5.44 g, 7.75 mmol). The metallic solids were washed with N,N-dimethylformamide (30 mL) and the washings added to the triflate/catalyst mixture, which was stirred at 50° C. overnight. The solution was concentrated under reduced pressure and the crude product slurried in water (500 mL) and 20% ethyl acetate in hexane (500 mL). The mixture was filtered and partitioned, and the aqueous layer re-extracted with 20% ethyl acetate in hexane (500 mL). The combined organic phases were washed with brine (500 mL), dried over MgSO$_4$, and concentrated under reduced pressure. The semi-crude product was obtained as a free running red-brown oil (81 g), which was purified twice by dry-flash chromatography (SiO$_2$, ethyl acetate and hexanes, 0 to 100%) followed by carbon treatment in 10% ethyl acetate/hexane to afford Intermediate (1b): $^1$H NMR (CDCl$_3$, 300 MHz): δ 5.50 (1H), 4.95 (1H), 4.40 (1H), 4.10 (2H), 3.77 (2H), 3.73 (3H), 2.50 (1H), 2.31 (1H), 2.07 (2H), 1.43 (9H).

Intermediate (1c): (R)-methyl 2-(tert-butoxycarbonyl)-3-(tetrahydro-2H-pyran-4-yl)propanoate

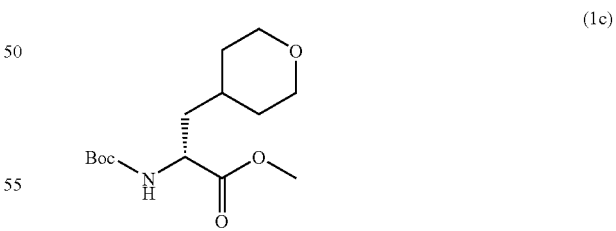
(1c)

In a stainless steel autoclave, 22.83 g (80.0 mmol) of Intermediate (1b) was dissolved in methanol (150 mL) to which was added a slurry of 5% Pd/C (2.3 g) in toluene (10 mL). The autoclave was charged to 20 bar with hydrogen and the reaction mixture was stirred for 2 hours at room temperature. The mixture was filtered through celite and the filtrates concentrated under reduced pressure to afford Intermediate (1c). The product was used in the next step without further purification.

¹H NMR (CDCl₃, 300 MHz): δ 4.92 (1H), 4.38 (1H), 3.92 (2H), 3.73 (3H), 3.35 (2H), 1.5-1.8 (4H), 1.43 (9H), 1.2-1.4 (2H).

Intermediate (1d): (R)-2-amino-3-(tetrahydro-2H-pyran-4-yl)propanoic acid

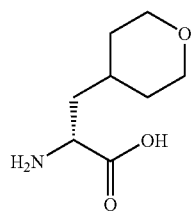

(1d)

Intermediate (1c) (22.9 g, 80.0 mmol) was suspended in 6N aqueous HCl (200 mL) and heated at 100° C. overnight. The mixture was cooled to room temperature and extracted with 20% ethyl acetate/hexane (100 mL) to remove any unwanted organics. The aqueous phase was concentrated under reduced pressure and co-distilled with toluene (2×200 mL) to afford the HCl salt of (1d), giving a yield of 17.9 g; 108% (off-white powder, presumed damp with water or toluene). ¹H NMR (d₆-DMSO, 300 MHz) δ 8.49 (3H), 3.79 (3H), 3.19 (2H), 2.44 (1H), 1.4-1.9 (5H), 1.12 (2H).

Secondly, the HCl salt of (1d) (11.6 g, 55.3 mmol) and isobutylene oxide (5.33 mL) were suspended in N,N-dimethylformamide (120 mL) in 4 Anton Paar 30 mL microwave vials. The mixtures were reacted at 100° C. for 1 hour and allowed to cool. The mixtures were washed out of the vials with ethyl acetate (50 mL each), combined and stirred briskly in further ethyl acetate (total volume 500 mL) for 10 minutes, during which time a thick cream-colored suspension formed. The solids were filtered off, broken up with a spatula and dried under vacuum oven at 50° C. overnight to afford Intermediate (1d).

Intermediate (1e): (R)-2-hydroxy-3-(tetrahydro-2H-pyran-4-yl)propanoic acid

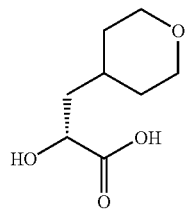

(1e)

Intermediate (1d) (7.68 g, 44.3 mmol) was dissolved in 1N H₂SO₄ (140 mL) and cooled to 0° C. under argon. NaNO₂ (4.6 g, 66.45 mmol) as a solution in water (25 mL) was introduced drop-wise under the surface of the mixture and the whole stirred overnight. The mixture was extracted with ethyl acetate (100 mL). The aqueous phase was extracted with further ethyl acetate (5×100 mL). The aqueous phase was cooled to 0° C. under argon and re-dosed with concentrated H₂SO₄ (3.5 mL) and NaNO₂ (4.6 g, 66.45 mmol) as a solution in water (25 mL) and stirred overnight. The mixture was extracted with ethyl acetate (6×100 mL), re-dosed as above, stirred overnight and finally extracted a third time with ethyl acetate (6×100 mL). All 1800 mL of organics were combined and stripped to afford Intermediate (1e) with a yield of 7.0 g (91%) as an orange oil. ¹H NMR (MeOD, 300 MHz): δ 4.20 (1H), 3.92 (2H), 3.39 (2H), 1.7 (2H), 1.6 (2H), 1.27 (2H).

Intermediate (1f): (R)-methyl 2-hydroxy-3-(tetrahydro-2H-pyran-4-yl)propanoate

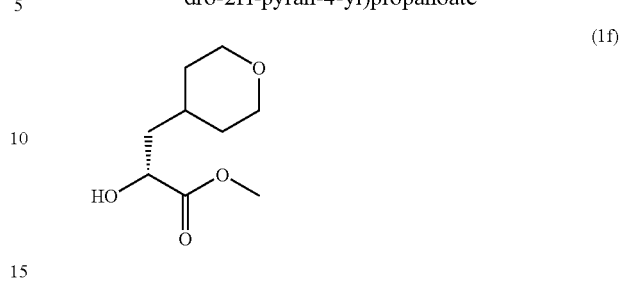

(1f)

Intermediate (1e) (9.0 g, 51 mmol) was dissolved in methanol (100 mL) and stirred. HCl was sparged in to the mixture for 15 minutes (exothermic 20 to 65° C.) and the whole was refluxed for 7 hours and allowed to cool. The mixture was stripped to approximately ⅓ volume, diluted with water (100 mL) and extracted with ethyl acetate (2×100 mL). The organics were stripped and the crude product purified by dry-flash chromatography (SiO₂, ethyl acetate and hexanes, 0 to 100%) to 3.8 g of Intermediate (1f). The aqueous phase was re-extracted with ethyl acetate (2×200 mL), stripped, and re-purified to a further 1.2 g of Intermediate (1f): ¹H NMR (CDCl₃, 300 MHz): δ 4.24 (1H), 3.95 (2H), 3.78 (3H), 3.39 (2H), 2.73 (1H), 1.83 (1H), 1.52-1.75 (4H), 1.22-1.42 (1H).

Intermediate (1g): (R)-methyl 3-(tetrahydro-2H-pyran-4-yl)-2-(trifluoromethylsulfonyloxy)-propanoate

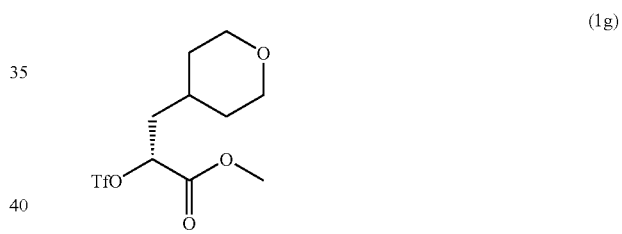

(1g)

Intermediate (1f) (1.21 g, 6.43 mmol) was dissolved in anhydrous dichloromethane (60 mL) under nitrogen. The mixture was stirred in an ice bath, and lutidine (1.6 mL) was added. Triflic anhydride (1.95 mL, 11.6 mmol) was added drop-wise, and the reaction was stirred for 60 minutes. The mixture was diluted with methyl tert-butyl ether, and washed 3-times with 3:1 brine/1N HCl. The organic layer was dried over MgSO₄, filtered, evaporated, and dried under high vacuum to afford Intermediate (1 g), which was utilized in the following reaction without further purification.

Intermediate (1h): 5-(trifluoromethyl)pyrazin-2(1H)-one

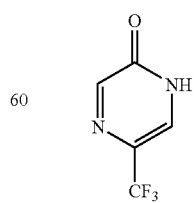

(1h)

Concentrated sulfuric acid (2.38 mL) was stirred in an ice bath. Sodium nitrite (199 mg) was added in one portion, and the mixture was stirred for 5 minutes and allowed to warm to room temperature over 5 minutes. It was then heated to 40° C. for 10 minutes and then cooled 0° C. A solution of 5-(trifluoromethyl)-pyrazin-2-amine (313 mg) in 3.4 mL concentrated sulfuric acid was added drop-wise over 5 minutes. The reaction was allowed to stir in the ice bath for 10 minutes, then at room temperature for 10 minutes, then at 40° C. for 20 minutes. The reaction was then pipetted into stirring ice water. The aqueous layer was extracted twice with ethyl acetate, which was then washed with water and brine and dried over MgSO₄. Purification by flash column chromatography (40 g, 0-100% ethyl acetate in heptanes) gave 0.239 g of Intermediate (1 h) as a white solid. MS 163.1 (M−1, APCI-).

Intermediate (1i): (S)-methyl 2-(2-oxo-5-(trifluoromethyl)pyrazin-1(2H)-yl)-3-(tetrahydro-2H-pyran-4-yl)propanoate

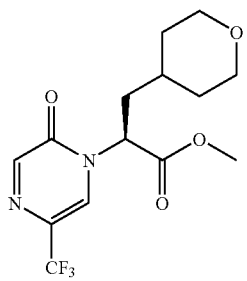

(1i)

Intermediate (1h) (150 mg) was stirred in 3 mL anhydrous THF at room temperature under nitrogen. A lithium bis(trimethylsilyl)amide solution (0.823 mL, 1.0 M in THF) was added. After 45 minutes, a solution of intermediate (1g) (293 mg) in 2 mL anhydrous THF was added. The reaction was stirred for 3 hours. The reaction was quenched with saturated ammonium chloride and extracted twice with ethyl acetate. The combined organic layers were dried over MgSO₄ and concentrated under reduced pressure. The resulting residue was purified (Combi-flash, Redi-sep 40 g, 0% ethyl acetate/heptane gradient to 100% ethyl acetate/heptane) to afford 28.8 mg of Intermediate (1i) as a clear oil. ¹H NMR (400 MHz, CDCl₃) δ 8.19 (1 H), 7.65 (1H), 5.64-5.68 (1 H), 3.92-3.96 (2 H), 3.79 (3 H), 3.23-3.38 (2 H), 2.06-2.18 (1 H), 1.79-1.90 (1 H), 1.22-1.75 (3 H); m/z 335.3 (M+H)⁺, 333.2 (M−H)⁻.

Intermediate (1j): (S)-benzyl 6-(2-(2-oxo-5-(trifluoromethyl)pyrazin-1(2H)-yl)-3-(tetrahydro-2H-pyran-4-yl)propanamido)nicotinate

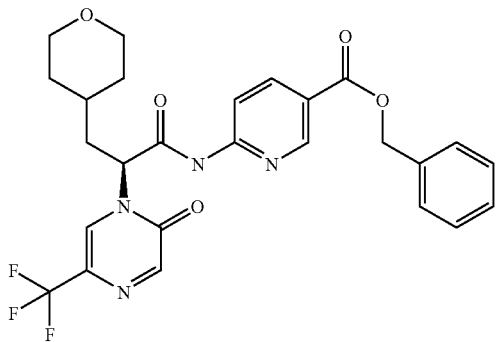

(1j)

To a solution of (1i) (444 mg) in dichloromethane (13.3 mL) was added (2e) (1.53 g). The mixture was purged with nitrogen and trimethyl aluminum (3.32 mL, 2.0 M in toluene) was then added dropwise. The reaction was heated to reflux for 8 hours. The reaction was then quenched with the slow addition of triethanolamine (2.20 mL). This solution was allowed to stir at room temperature for 15 min. The mixture was diluted with 25 mL of dichloromethane and 20 mL of water. The layers were separated and the aqueous layer was extracted again with dichloromethane. The combined organics were washed with water and brine, dried over Na₂SO₄, filtered, and concentrated. Column chromatography, eluting with a gradient of 10-50% ethyl acetate in heptane, afforded (1j) (229 mg, 32.5% yield) as a pale yellow solid. ¹H NMR (400 MHz, CDCl₃) δ ppm 1.32-1.50 (4 H), 1.59-1.76 (2 H), 1.84-1.97 (1 H), 2.23 (1 H), 3.24-3.40 (2 H), 3.93 (2 H), 5.35 (2 H), 5.85 (1 H), 7.28-7.47 (5 H), 8.13 (1 H), 8.30 (1 H), 8.36 (1 H), 8.91 (1 H), 9.38 (1 H). m/z 531.5 (M+H)⁺.

Intermediate (2a): (R)-methyl 3-cyclopentyl-2-hydroxypropanoate

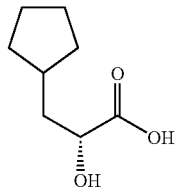

(2a)

To a stirred solution of (R)-2-amino-3-cyclopentylpropanoic acid (5.0 g) (Amatek Chemical Company, Ltd., Hong Kong) and 1 M H₂SO₄ (45.1 mL) at 0° C., was added a solution of NaNO₂ (3.12 g) in water (15.6 mL) drop wise over 10 minutes. The reaction mixture was stirred for 3 hours at 0° C., then for 2 hours at room temperature. The solution was then extracted 3-times with ether. The combined organic extracts were dried over MgSO₄, filtered, and the filtrate was concentrated to afford 2.36 g of Intermediate (2a). ¹H NMR (400 MHz, CDCl₃) δ 4.26-4.28 (1 H), 1.99-2.07 (1 H), 1.76-1.81 (4 H), 1.60-1.62 (4 H), 1.12-1.16 (2 H); m/z 157.1 (M−H)⁻.

Intermediate (2b): (R)-methyl 3-cyclopentyl-2-hydroxypropanoate

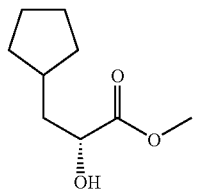

(2b)

To a stirred solution of 2.36 g of Intermediate (2a) in anhydrous methanol (15 mL) at room temperature was added SOCl₂ (1.64 mL). The resulting mixture was heated at reflux for 2 hours. It was then cooled and concentrated under reduced pressure. The residue was partitioned between ethyl acetate and aqueous saturated NaHCO₃ solution. The biphasic mixture was separated and the aqueous portion was extracted with ethyl acetate. The combined extracts were dried over MgSO₄, filtered, and the filtrate concentrated under reduced pressure. The resulting residue was purified by flash column chromatography (silica gel, heptanes/ethyl acetate) to afford 1.5 g of Intermediate (2b) as a clear oil. $^1$H NMR (400 MHz, CDCl$_3$) δ 4.15-4.20 (1 H), 3.77 (3H), 2.62-2.63 (1 H), 1.97-2.05 (1 H), 1.49-1.86 (8 H), 1.06-1.17 (2 H); m/z 171.6 (M)$^+$.

Intermediate (2c): (R)-methyl 3-cyclopentyl-2-(trifluoromethylsulfonyloxy)propanoate

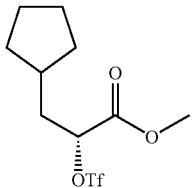

(2c)

To a stirred solution of 50 mg of Intermediate (2b) in anhydrous methylene chloride (3 mL) at 0° C. under nitrogen was added 2,6-lutidine (0.064 mL) followed by drop wise trifluoro-methanesulfonic anhydride (0.083 mL). After stirring for 45 minutes at the same temperature, methyl tert-butyl ether was added and the mixture was thoroughly washed three-times with a mixture of brine and aqueous 1N HCl (3:1). The organic extracts were dried over MgSO$_4$, filtered, and the filtrate concentrated to afford Intermediate (2c) as a tan oil. $^1$H NMR (400 MHz, CDCl$_3$) δ 5.09-5.12 (1 H), 3.81 (3 H) 1.97-2.09 (1 H), 1.70-1.96 (4 H), 1.47-1.66 (4 H), 1.03-1.19 (2 H).

Intermediate (2d): (S)-methyl 2-(2-oxo-5-(trifluoromethyl)pyrazin-1(2H)-yl)-3-cyclopentyl propanoate

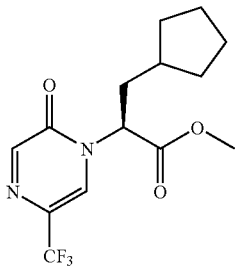

(2d)

Intermediate (1h) (489 mg) was stirred in 15 mL anhydrous THF at room temperature under nitrogen. A lithium bis(trimethylsilyl)amide solution (2.7 mL, 1.0 M in THF) was added. After 50 minutes, a solution of intermediate (1l) (907 mg) in 5 mL anhydrous THF was added. The reaction was stirred for 2 hours. The reaction was quenched with saturated ammonium chloride and extracted twice with ethyl acetate. The combined organic layers were washed with brine and then were dried over MgSO$_4$ and concentrated under reduced pressure. The resulting residue was purified (Combi-flash, Redi-sep 40 g, 100% heptane gradient to 1:1 ethyl acetate/heptane) to afford 948 mg of Intermediate (2d). $^1$H NMR (400 MHz, Chloroform-d) δ ppm 8.17 (1 H), 7.66 (1 H), 5.51 (1 H), 3.77 (3 H) 2.11-2.18 (1 H), 1.98 (1 H), 1.77 (2 H), 1.47-1.67 (6 H), 1.06-1.23 (2 H).

Intermediate (2e): benzyl 6-aminonicotinate

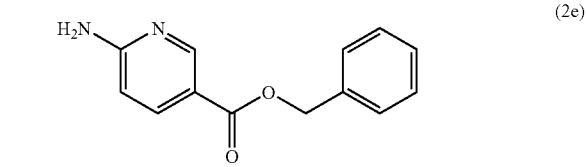

(2e)

6-aminonicotinic acid (3.0 g, 22 mmol) and 4-toluenesulfonic acid monohydrate (9.09 g, 47.8 mmol) were heated to 120° C. in benzyl alcohol (100 ml) for 20 hours under nitrogen. The resulting yellow solution was cooled to room temperature and poured into stirring diethyl ether (500 ml) and water (300 ml). 1N HCl was added to insure strong acidity. The ether layer was separated, and the aqueous layer was washed with ether. Solid potassium carbonate was added in portions with stirring to the aqueous layer to pH 10, creating a precipitate. Ethyl acetate was added to dissolve the solid. The aqueous layer was separated and extracted with ethyl acetate. The combined organics were washed with brine, dried over sodium sulfate, filtered, and evaporated. The crude residue was purified (Combi-flash, Redi-sep 80 g, 75% ethyl acetate/heptane) to afford Intermediate (2e) (1.81 g, 7.93 mmol, 37%). $^1$H NMR (400 MHz, d$_6$DMSO) δ 8.51 (d, 1H), 7.82 (d, 1 H), 7.28-7.42 (5 H), 6.83 (2 H), 6.43 (1 H), 5.24 (2 H); m/z 229.2 (M+H)$^+$.

Intermediate (2f): (S)-benzyl 6-(3-cyclopentyl-2-(2-oxo-5-(trifluoromethyl)pyrazin-1(2H)-yl)propanamido)nicotinate

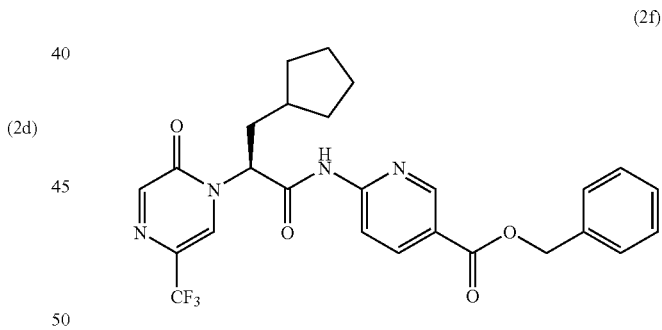

(2f)

Intermediate (2e) (277 mg) was stirred in 5 mL anhydrous 1,2-dimethoxyethane. Dimethylaluminium chloride solution (1.65 mL, 1.0M in hexane) was added, and the reaction was stirred at room temperature for 30 minutes. A solution of Intermediate (2d), (75 mg) in 3 mL anhydrous 1,2-dimethoxyethane was added and the reaction was stirred at 80° C. for 24 hours. The reaction was cooled and saturated aqueous Rochelle's salt was added and stirred for 5 minutes. The resulting aqueous slurry was extracted twice with dichloromethane. The combined organic layers were dried over MgSO$_4$ and concentrated under reduced pressure. The resulting residue was purified (Combi-flash, Redi-sep 40 g, 0% ethyl acetate/heptane gradient to 100% ethyl acetate/heptane) to afford Intermediate (2f) (35 mg) as a white solid. $^1$H NMR (400 MHz, CDCl$_3$) δ 9.73 (1H), 8.92 (1H), 8.41 (1H), 8.31 (1H), 8.17 (1H), 8.03 (1H), 7.34-7.41 (5H), 5.86-5.99 (1H), 5.35 (2H), 2.25-2.28 (1 H), 2.00-2.01 (1 H), 1.47-1.87 (7 H), 1.16-1.27 (2 H). m/z 514 (M−H)⁻.

Intermediate (3a): (R)-methyl 3-cyclohexyl-2-(trifluoromethylsulfonyloxy)propanoate

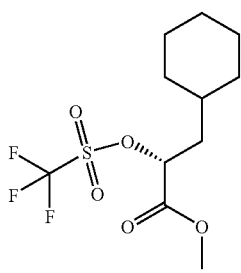

(3a)

(R)-methyl 3-cyclohexyl-2-hydroxypropanoate (Organic Process Research & Development 7(4) 559-570; 2003) (250 mg) was dissolved in dichloromethane (5 mL) and cooled to 0° C. A solution of 2,6-lutidine (300 mg) in 0.5 mL dichloromethane was added; subsequently, bis(trifluoromethanesulfonic) anhydride (0.41 mL) was slowly added. The reaction was allowed to stir for one hour, gradually warming to 25° C. The reaction was then diluted with 35 mL of methyl tert-butylether and washed with a 3:1 solution of brine and 1N HCl (3×15 mL). The organics were dried over Na₂SO₄, filtered, and concentrated to give Intermediate (3a) (427 mg, 100% yield) as a yellow oil. ¹H NMR (400 MHz, CDCl₃) δ 0.84-1.05 (2H), 1.09-1.34 (4H), 1.59-1.75 (4H), 1.75-1.85 (2H), 1.85-1.98 (1H), 3.83 (3H) 5.18 (1H).

Intermediate (3b): (S)-methyl 3-cyclohexyl-2-(2-oxo-5-(trifluoromethyl)pyrazin-1(2H)-yl)propanoate

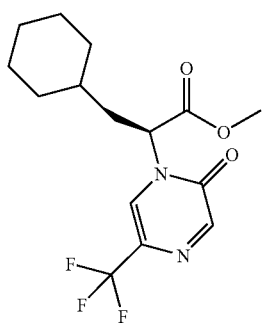

(3b)

The title compound was prepared by a method analogous to that described for Intermediate (1i), using Intermediate (3a) as the starting material. ¹H NMR (400 MHz, CDCl₃) δ 0.87-1.02 (2 H), 1.04-1.21 (4 H), 1.68 (4 H), 1.79 (2 H), 1.99-2.10 (1 H), 3.73 (3 H). 5.61 (1 H), 7.64 (1 H), 8.17 (1 H). m/z 333.4 (M+H)⁺.

Intermediate (3c): (S)-benzyl 6-(3-cyclohexyl-2-(2-oxo-5-(trifluoromethyl)pyrazin-1(2H)-yl)propanamido)nicotinate

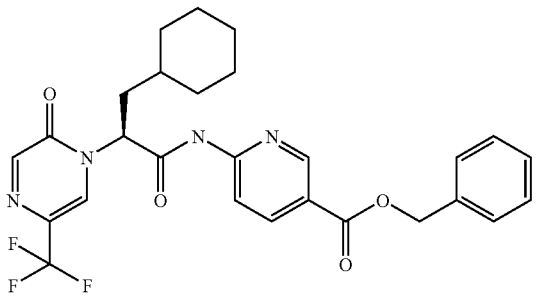

(3c)

The title compound was prepared by a method analogous to that described for Intermediate (1j), using Intermediate (3b) as the starting material. ¹H NMR (400 MHz, CDCl₃) δ 1.16 (2 H), 1.20-1.33 (4 H), 1.60-1.72 (3 H), 1.76 (2 H), 1.84 (1 H), 2.15 (1 H), 5.35 (2 H), 5.80 (1 H), 7.31-7.46 (5 H), 7.92 (1 H), 8.14 (1 H), 8.28-8.32 (1 H), 8.33 (1 H), 8.93 (1 H), 9.27 (1 H). m/z 529.5 (M+H)⁺.

Intermediate (4a): (R)-methyl 4-methyl-2-(trifluoromethylsulfonyloxy)pentanoate

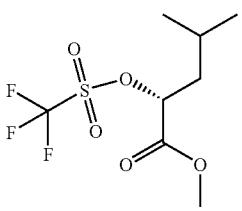

(4a)

The title compound was prepared by a method analogous to that described for Intermediate (3a), using (R)-methyl 2-hydroxy-4-methylpentanoate (JACS 112(10), 3949-54; 1990) as the starting material. ¹H NMR (400 MHz, CDCl₃) δ 0.85-1.07 (6 H), 1.69-1.87 (2 H), 1.87-2.03 (1 H), 3.83 (3 H), 5.15 (1 H).

Intermediate (4b): (S)-methyl 4-methyl-2-(2-oxo-5-(trifluoromethyl)pyrazin-1(2H)-yl)pentanoate

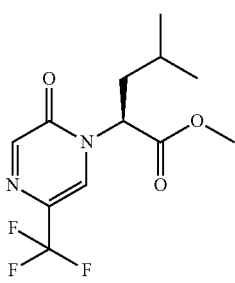

(4b)

The title compound was prepared by a method analogous to that described for Intermediate (1i), using (4a) as the starting material. ¹H NMR (400 MHz, CDCl₃) δ 0.96 (6 H), 1.36-1.50

(1 H), 1.74-1.93 (1 H), 1.93-2.11 (1 H), 3.78 (3 H), 5.59 (1 H), 7.64 (1 H), 8.17 (1 H). m/z 293.4 (M+H)⁺.

Intermediate (4c): (S)-benzyl 6-(4-methyl-2-(2-oxo-5-(trifluoromethyl)pyrazin-1(2H)-yl)pentanamido)nicotinate

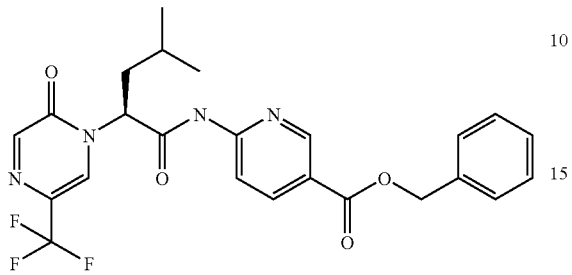

(4c)

The title compound was prepared by a method analogous to that described for Intermediate (1j), using Intermediate (4b) as the starting material and dichloroethane as solvent. ¹H NMR (400 MHz, CDCl₃) δ 1.00 (6 H), 1.50-1.60 (1 H), 1.81-1.93 (1 H), 2.11 (1 H), 5.36 (2 H), 5.76 (1 H), 7.33-7.39 (5 H), 7.92 (1 H), 8.14 (1 H), 8.27-8.36 (2 H), 8.93 (1 H), 9.21 (1 H). m/z 489.5 (M+H)⁺.

Intermediate (5a): (S)-3-cyclopentyl-2-(2-oxo-5-(trifluoromethyl)pyrazin-1(2H)-yl)propanoic acid

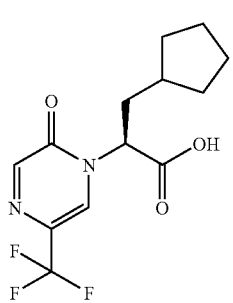

(5a)

A mixture of Intermediate (2d) (230 mg) in 6N HCl (4.0 mL) was heated to 95° C. for 20 hours. The reaction was cooled to room temperature and the pH adjusted to 4 by the addition of 5N NaOH. The solution was extracted three times using 10% 2-propanol/dichloromethane. The combined organics were dried over Na₂SO₄, filtered, and concentrated to afford the desired product Intermediate (5a) (220 mg, 100% yield) as a yellow oil. ¹H NMR (400 MHz, CDCl₃) δ 1.06-1.16 (1 H), 1.46-1.56 (2 H), 1.57-1.70 (3 H), 1.70-1.86 (2 H), 2.01 (1 H), 2.14-2.27 (1 H), 4.23 (2 H), 5.51 (1 H), 7.62 (1 H), 8.19 (1 H). m/z 303.4 (M+H)⁺.

Intermediate (5b): benzyl 2-(6-aminopyridin-3-yl)acetate

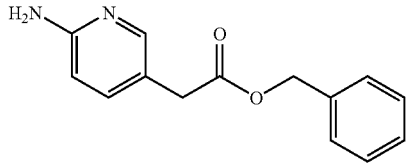

(5b)

Ethyl 2-(6-aminopyridin-3-yl)acetate (described in WO 2009/091014) (1.5 g) was dissolved in benzyl alcohol (10 mL). Titanium(IV) ethoxide (1.74 mL) was added and the reaction was heated to 110° C. for 16 hours. The reaction was cooled to room temperature and quenched with 1N HCl. This mixture was basified with saturated sodium bicarbonate and extracted three times with ethyl acetate. The combined organics were dried over MgSO₄, filtered, and concentrated. Purification by column chromatography, eluting with a gradient of 30-100% ethyl acetate in heptane, afforded the title compound Intermediate (5b) (1.04 g, 51% yield) as a white solid. ¹H NMR (400 MHz, CDCl₃) δ 3.51 (2 H), 4.37 (2 H), 5.11 (2 H), 6.46 (1 H), 7.27-7.41 (6 H), 7.95 (1H). m/z 243.4 (M+H)⁺.

Intermediate (5c): (S)-benzyl 2-(6-(3-cyclopentyl-2-(2-oxo-5-(trifluoromethyl)pyrazin-1(2H)-yl)propanamido)pyridin-3-yl)acetate

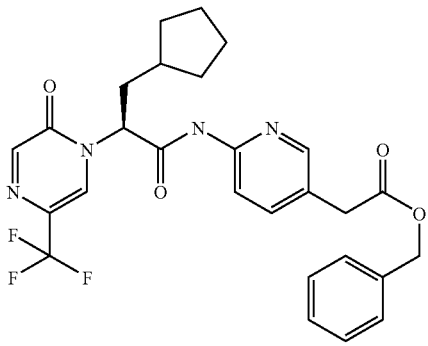

(5c)

Intermediate (5a) (100 mg) was dissolved in dichloromethane (3.29 mL) and N,N-dimethylformamide (one drop) was added followed by oxalyl chloride (93 uL). The reaction mixture was then stirred at 25° C. for 1 hour. The mixture was subsequently concentrated and dichloroethane was added and evaporated two times. The resulting residue was dissolved in dichloromethane (3.0 mL). Intermediate (5b) (87.7 mg) and pyridine (56 uL) were added and the reaction was stirred at 25° C. for 3 hours. Diisopropylethylamine (0.20 mL) was then added along with a catalytic amount of 4-dimethylaminopyridine and the reaction was stirred at 25° C. for 16 hours. Subsequently, additional dichloroethane (2.0 mL) was added and the reaction was heated to 60° C. for an additional 16 hours. The reaction was then cooled to room temperature and diluted with ethyl acetate. The solution was washed with water, dried over MgSO₄, filtered, and concentrated. Purification by column chromatography, eluting with a gradient of 0-50% ethyl acetate in heptane, afforded the title compound Intermediate (5c) (83 mg, 48% yield) as a yellow solid. ¹H NMR (400 MHz, CDCl₃) δ 1.11-1.22 (2 H), 1.25 (1 H), 1.46-1.57 (2 H), 1.63 (2 H), 1.72 (1 H), 1.81 (1 H), 1.89-2.01 (1 H), 2.26 (1 H), 3.63 (2 H), 5.12 (2 H), 5.57 (1 H), 7.27-7.39 (5 H), 7.64 (1 H), 7.92 (1 H), 8.05 (1 H), 8.20 (1 H), 8.24 (1 H) 8.67 (1 H). m/z 529.6 (M+H)⁺.

Intermediate (6a): (R)-2-amino-3-cyclobutylpropanoic acid

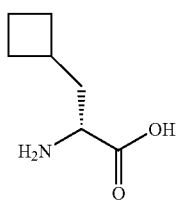

(6a)

(R)-2-(tert-butoxycarbonylamino)-3-cyclobutylpropanoate diisopropylamine salt (5.00 g) (available from Chem-Impex International, Wood Dale, Ill.) was dissolved in dichloromethane (50 mL) and washed twice with 0.25M sulfuric acid. The organic layer was dried over $Na_2SO_4$, filtered, and concentrated to give 3.98 g of a clear colorless oil. This residue was dissolved in dichloromethane (12.0 mL) and treated with trifluoroacetic acid (10.0 mL). The reaction was stirred at room temperature for 3 hours and then concentrated. The clear, colorless oil was triturated with diethyl ether to yield the TFA salt of the desired product (6a) (3.73 g, 100% yield) as a white crystalline solid. $^1$H NMR (400 MHz, DMSO-d6) δ 1.50-1.67 (2 H), 1.68-1.93 (4 H), 2.01 (2 H), 2.33-2.44 (1 H), 3.70 (1 H).

Intermediate (6b): (R)-methyl 3-cyclobutyl-2-hydroxypropanoate

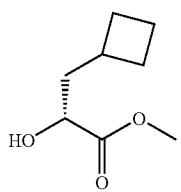

(6b)

A solution of Intermediate (6a) (3.79 g) in 2N $H_2SO_4$ (22 mL) was cooled to 0° C. A solution of sodium nitrite (1.52 g) in water (8 mL) was added dropwise over 30 min. The reaction was stirred at 0° C. for 3 hours, and then was allowed to gradually warm to 25° C. and stir overnight. The reaction was extracted with methyl tert-butylether twice. The combined organics were dried over $MgSO_4$, filtered, and concentrated to an oil. This residue was dissolved in anhydrous methanol (8.0 mL). Thionyl chloride (1.10 mL) was added and the reaction was refluxed for 30 min. The reaction was then cooled to room temperature and concentrated. The residue was partitioned between ethyl acetate and saturated sodium bicarbonate. The layers were separated and the aqueous was extracted again with ethyl acetate. The combined organics were dried over $MgSO_4$, filtered, and concentrated to an oil. Column chromatography, using a gradient of 0-40% ethyl acetate in heptane afforded the title compound (6b) (656 mg, 40% yield) as a clear oil. $^1$H NMR (400 MHz, CDCl$_3$) δ ppm 1.54-1.93 (6 H), 1.97-2.12 (2 H), 2.43-2.57 (1 H), 3.76 (3 H), 4.11 (1 H).

Intermediate (6c): (S)-methyl 3-cyclobutyl-2-(2-oxo-5-(trifluoromethyl)pyrazin-1(2H)-yl)propanoate

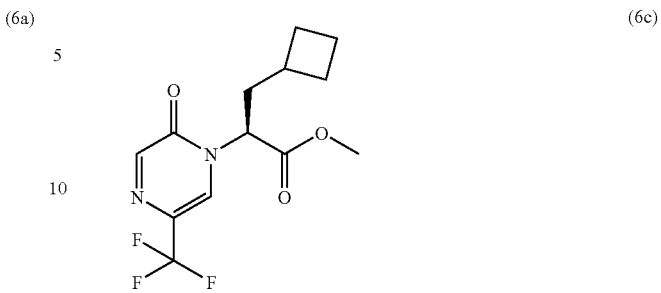

(6c)

Intermediate (6b) (656 mg) was dissolved in dichloromethane (8.0 mL) and cooled to 0° C. 2,6-lutidine (0.912 mL) was added, followed by the dropwise addition of trifluoromethanesulfonic anhydride (1.18 mL) over 20 min. The solution was stirred at 0° C. for 40 min. The reaction was concentrated, the resulting residue diluted with methyl tert-butylether (30 mL), and washed three times with 0.25M $H_2SO_4$. The organics were dried over $MgSO_4$, filtered, and concentrated to give a reddish oil. This material was used directly in the next step.

Lithium bis(trimethylsilyl)amide (0.914 mL, 1.0M in THF) was added to a stirred solution of Intermediate (1h) (165 mg) in anhydrous tetrahydrofuran (4.5 mL). This solution was cooled to −5° C. and stirred for 35 min. A solution of the above prepared triflate (292 mg) in tetrahydrofuran (4.5 mL) was then added. The reaction was allowed to warm to room temperature and stir for 2.5 hours. The reaction was then quenched with saturated ammonium chloride, diluted with brine, and extracted twice with ethyl acetate. The organics were dried over $MgSO_4$, filtered, and concentrated to give an oil. Purification by column chromatography, eluting with a gradient of 0-60% ethyl acetate in heptane, afforded the desired product (6c) (222 mg, 73% yield) as a clear oil. $^1$H NMR (400 MHz, CDCl$_3$) δ 1.58-1.75 (2 H), 1.76-1.91 (2 H), 1.92-2.02 (2 H), 2.04 (1 H), 2.12-2.23 (1 H), 2.23-2.31 (1 H), 3.77 (3 H), 5.37 (1 H), 7.63 (1 H), 8.15 (1 H). m/z 305.4 $(M+H)^+$.

Intermediate (6d): (S)-benzyl 6-(3-cyclobutyl-2-(2-oxo-5-(trifluoromethyl)pyrazin-1(2H)-yl)propanamido)nicotinate

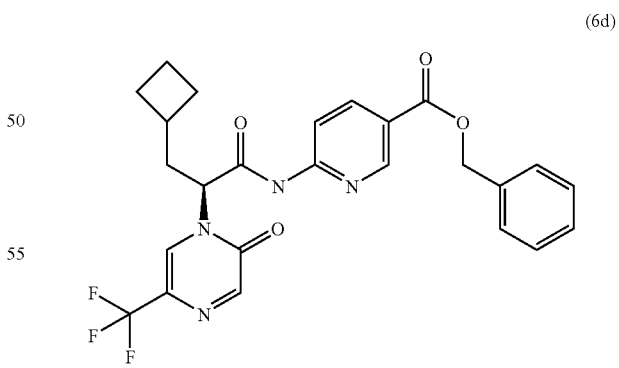

(6d)

Intermediate (6c) (222 mg) was dissolved in dichloroethane (7.2 mL). Intermediate (2e) (832 mg) was added and the solution was purged with nitrogen. Trimethyl aluminum (1.81 mL, 2.0 M in hexanes) was added dropwise, and the resulting reaction mixture was heated to 60° C. for 5 hours. The reaction was cooled to room temperature and left stirring for 16 hours. To quench the reaction, 6 mL of saturated Rochelle salt were added and the resulting mixture was allowed to stir for 30 min. The solution was diluted with ethyl acetate and washed with water. The aqueous was extracted again with ethyl acetate. The combined organics were washed with brine, dried over MgSO4, filtered, and concentrated to a solid. Column chromatography, eluting with a gradient of 0-50% ethyl acetate in heptane, afforded the title compound (6d) (204 mg, 56% yield) as a yellow oil. ¹H NMR (400 MHz, CDCl₃) δ 1.64-1.76 (3 H), 1.77-1.92 (2 H), 2.04-2.12 (2 H), 2.21-2.40 (2 H), 5.35 (1 H), 5.60 (1 H), 7.32-7.45 (5 H), 7.95 (1 H), 8.15 (1 H), 8.28-8.34 (2 H), 8.93 (1 H). m/z 501.5 (M+H)⁺.

Example 1

(S)-N-(5-methylpyridin-2-yl)-2-(2-oxo-5-(trifluoromethyl)pyrazin-1(2H)-yl)-3-(tetrahydro-2H-pyran-4-yl)propanamide, (1)

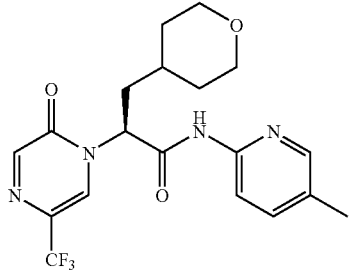

(1)

2-amino-5-picoline (available from Sigma-Aldrich, St. Louis, Mo.) (27.9 mg) was stirred in 3 mL anhydrous toluene. Trimethylaluminum solution (0.129 mL, 2.0 M in toluene) was added, and the reaction was stirred at room temperature for 35 minutes. A solution of (1i-1) in 2 mL anhydrous 1,2-dichloroethane was added and the reaction was stirred at 80° C. for 24 hours. The reaction was cooled and saturated aqueous Rochelle's salt was added and stirred for 5 minutes. This was extracted twice with dichloromethane. The combined organic layers were dried over MgSO₄ and concentrated under reduced pressure. The resulting residue was purified (Combi-flash, Redi-sep 40 g, 0% ethyl acetate/heptane gradient to 100% ethyl acetate/heptane) to afford Example 1 (19.4 mg) as a white solid. ¹H NMR (400 MHz, CDCl₃) δ 8.66 (1 H), 8.12 (1 H), 8.07 (1 H), 7.91 (1 H), 7.48-7.53 (2 H), 5.63-5.70 (1 H), 3.92-3.95 (2 H), 3.28-3.33 (2 H), 2.03-2.27 (4 H), 1.85-1.90 (1 H), 1.62-1.68 (2 H), 1.25-1.55 (3 H); LCMS for $C_{19}H_{21}F_3N_4O_3$ m/z 411.2 (M+H)⁺, 409.2 (M−H)⁻.

Example 2

(S)-6-(3-cyclopentyl-2-(2-oxo-5-(trifluoromethyl)pyrazin-1(2H)-yl)propanamido)nicotinic acid, (2)

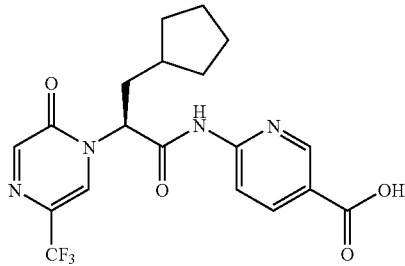

(2)

Intermediate (2f) (30 mg) was taken up in 30 mL of methanol and was injected onto a H-Cube automatic hydrogenation system (available from ThalesNano Nanotechnology Inc., Budapest, Hungary). Hydrogenation occurred under a continuous flow of hydrogen on a 10% Pd/C cartridge at a flow rate of 1 mL per minute. The filtrate was collected and concentrated. The resulting crude white solid was dissolved in dichloromethane and washed with water. The combined organic layers were dried over MgSO₄ and concentrated under reduced pressure to afford 5 mg of Example 2 as a white solid. ¹H NMR (400 MHz, CDCl₃) δ 8.96 (1H), 8.48-8.52 (2H), 8.24 (1H), 7.87 (1H), 5.85 (1H), 2.21-2.01 (2 H), 1.46-1.84 (7 H), 1.16-1.27 (2 H). m/z 423 (M−H)⁻.

Example 3

(S)-3-cyclopentyl-2-(2-oxo-5-(trifluoromethyl)pyrazin-1(2H)-yl)-N-(pyrazin-2-yl)propanamide, (3)

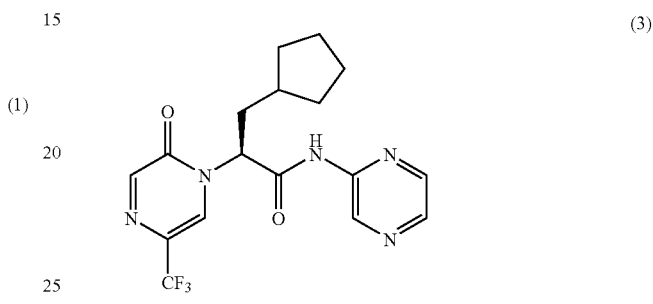

(3)

Aminopyrazine (89.6 mg) was stirred in 1.5 mL anhydrous toluene. Trimethylaluminum solution (0.515 mL, 2.0 M in toluene) was added, and the reaction was stirred at room temperature for 45 minutes. A solution of 150 mg of (2d) in 3 mL anhydrous 1,2-dichloroethane was added and the reaction was stirred at 80° C. for 24 hours. The reaction was cooled and saturated aqueous Rochelle's salt was added and stirred for 45 minutes. This was extracted twice with dichloromethane. The combined organic layers were dried over MgSO₄ and concentrated under reduced pressure. The resulting residue was purified by preparative HPLC (H₂O/20% acetonitrile linear to 5% H₂O/95% acetonitrile over 6 minutes, then 5% H₂O/95% acetonitrile to 7.5 minutes using a Waters XTerra MS C18 5μ column) with ammonium hydroxide 0.03% as a modifier to afford Example 3 (69.5 mg) as a white solid. ¹H NMR (400 MHz, CDCl₃) δ 9.89 (1 H), 9.42 (1 H), 8.45 (1 H), 8.36 (1 H), 8.24 (1 H), 8.10 (1 H), 5.95-5.99 (1 H), 2.26-2.34 (1 H), 1.96-2.03 (1 H), 1.47-1.87 (7 H), 1.16-1.27 (2 H); m/z 382.19 (M+H)⁺.

Example 4

(S)-3-cyclopentyl-N-(5-methylpyridin-2-yl)-2-(2-oxo-5-(trifluoromethyl)pyrazin-1(2H)-yl)propanamide, (4)

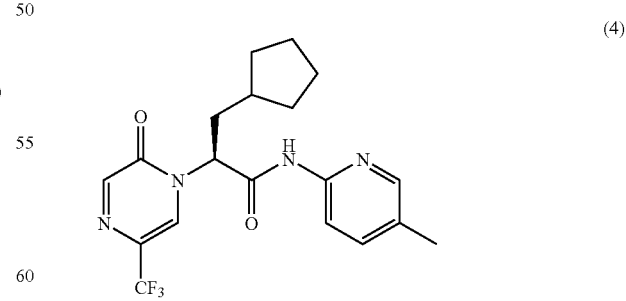

(4)

2-amino-5-picoline (102 mg) was stirred in 1.5 mL anhydrous toluene. Trimethylaluminum solution (0.527 mL, 2.0 M in toluene) was added, and the reaction was stirred at room temperature for 45 minutes. A solution of 150 mg of Intermediate (2d) in 3 mL anhydrous 1,2-dichloroethane was added and the reaction was stirred at 80° C. for 24 hours. The reaction was cooled and saturated aqueous Rochelle's salt was added and stirred for 45 minutes. This was extracted twice with dichloromethane. The combined organic layers were dried over MgSO$_4$ and concentrated under reduced pressure. The resulting residue was purified by preparative HPLC (Hold 95% water/5% acetonitrile (initial conditions) linear gradient to 1.0 minute, ramp to 5% water/95% acetonitrile at 10.0 minutes, hold 5% water/95% acetonitrile to 12.5 minutes, with formic acid 0.1% modifier. Preparative column: Phenomenex Luna (2) C-18 150×4.6 mm, 5μ) (Combi-flash, Redi-sep 40 g, 0% ethyl acetate/heptane gradient to 100% ethyl acetate/heptane) to afford Example 3 (91.8 mg) as a white solid. $^1$H NMR (400 MHz, CDCl$_3$) δ 9.75 (1 H), 8.38 (1 H), 8.15 (1 H), 8.09 (1 H), 7.97-7.99 (1 H), 7.49-7.51 (1 H), 5.80-5.84 (1 H), 2.28 (3 H), 2.18-2.25 (1 H), 1.91-1.99 (1 H), 1.44-1.83 (7 H), 1.09-1.19 (2 H); m/z 395.1 (M+H)$^+$.

Example 5

(S)-6-(3-cyclohexyl-2-(2-oxo-5-(trifluoromethyl) pyrazin-1(2H)-yl)propanamido)nicotinic acid, (5)

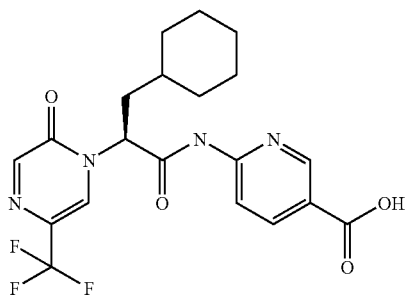

(5)

Intermediate (3c) (30 mg) was dissolved in ethanol (1.0 mL) and acetic acid (30 uL) and 10% palladium on carbon (3 mg) were added. The reaction vessel was pressurized with hydrogen gas (15 psi) and agitated at 25° C. for 2 hours. The reaction was then filtered and concentrated to afford (5) (21 mg, 84% yield) as a white solid. $^1$H NMR (400 MHz, methanol-d4) δ 1.03 (2 H), 1.18 (4 H), 1.58-1.77 (4 H), 1.77-1.86 (1 H), 1.99-2.16 (2 H), 5.83-5.93 (1 H), 8.09-8.18 (2 H), 8.20 (1 H), 8.29 (1 H) 8.89, (1 H). m/z 439.5 (M+H)$^+$.

Example 6

(S)-6-(2-(2-oxo-5-(trifluoromethyl)pyrazin-1(2H)-yl)-3-(tetrahydro-2H-pyran-4-yl)propanamido)nicotinic acid, (6)

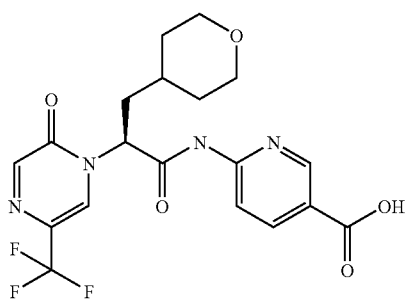

(6)

The title compound was prepared by a method analogous to that described for Example 5, using Intermediate (1j) as the starting material. $^1$H NMR (400 MHz, methanol-d$_4$) δ 1.23-1.48 (4 H), 1.62 (1 H), 1.65-1.74 (1 H), 2.01-2.13 (1 H), 2.13-2.24 (1 H), 3.31-3.38 (1 H), 3.81-3.92 (2 H), 5.90 (1 H), 8.06 (1 H), 8.09-8.13 (1 H), 8.24 (1 H), 8.26 (1 H), 8.85 (1 H). m/z 441.1 (M+H)$^+$.

Example 7

(S)-6-(4-methyl-2-(2-oxo-5-(trifluoromethyl) pyrazin-1(2H)-yl)pentanamido)nicotinic acid, (7)

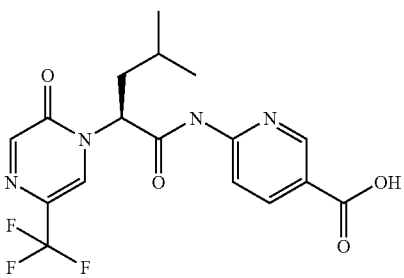

(7)

The title compound was prepared by a method analogous to that described for Example (5), using Intermediate (4c) as the starting material. $^1$H NMR (400 MHz, methanol-d$_4$) δ 0.92-1.04 (6 H), 1.99 (1 H), 2.10-2.21 (1 H), 5.80-5.92 (1 H), 8.08-8.15 (2 H), 8.20 (1 H), 8.27 (1 H), 8.29 (1 H), 8.88 (1 H). m/z 399.5 (M+H)$^+$.

Example 8

(S)-2-(6-(3-cyclopentyl-2-(2-oxo-5-(trifluoromethyl) pyrazin-1(2H)-yl)propanamido)pyridin-3-yl)acetic acid, (8)

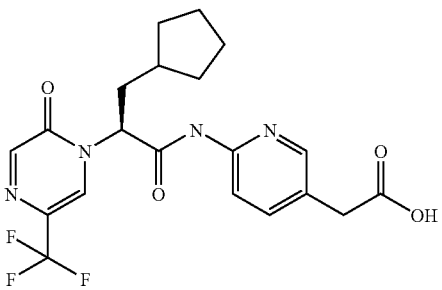

(8)

The title compound was prepared by a method analogous to that described for Example (5), using Intermediate (5c) as the starting material. $^1$H NMR (400 MHz, methanol-d$_4$) δ 1.11-1.23 (1 H), 1.24-1.37 (2 H), 1.46-1.58 (2 H), 1.58-1.72 (3 H), 1.78 (2 H), 2.09-2.27 (2 H), 3.60 (2 H), 5.77 (1 H), 7.70 (1 H), 7.98 (1 H), 8.11 (1 H), 8.19-8.26 (2 H). m/z 439.5 (M+H)$^+$.

Example 9

(S)-6-(3-cyclobutyl-2-(2-oxo-5-(trifluoromethyl) pyrazin-1(2H)-yl)propanamido)nicotinic acid, (9)

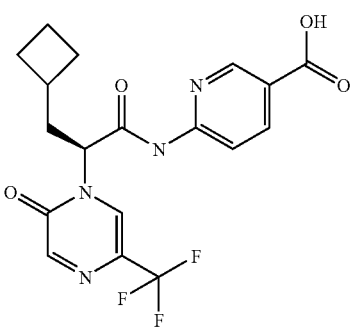

(9)

The title compound was prepared by a method analogous to that described for Example (5), using Intermediate (6d) as starting material. $^1$H NMR (400 MHz, DMSO-$d_6$) δ 1.55 (1 H), 1.65-1.89 (5 H), 2.07-2.26 (2 H), 2.28-2.40 (1 H), 5.57-5.65 (1 H), 8.07 (1 H), 8.13 (1 H), 8.23 (1 H), 8.32 (1 H), 8.83 (1 H), 11.50 (1 H), 13.14 (1 H). m/z 411.5 (M+H)$^+$.

Biological Assays

Representative compounds of this invention were evaluated in biochemical assays (Assay 1 or Assay 2) to characterize their glucokinase activation properties. The recombinant human glucokinase protein utilized in both assays was prepared and purified as described below.

Beta Cell Glucokinase His-Tag Growth and Induction Conditions: BL21(DE3) cells (Invitrogen Corporation, Carlsbad, Calif.) containing pBCGK (C or N His) vector were grown at 37° C. (in 2XYT) until the OD600 was between 0.6-1.0. Expression was induced by addition of isopropylthiogalactoside to a final concentration of 0.1-0.2 mM to the cells which were then incubated overnight at 23° C. The next day, cells were harvested via centrifugation at 5000 rpm for 15 minutes at 4° C. The cell pellet was stored at −80° C. for future purification.

Beta Cell Glucokinase His-Tag Purification Conditions: A Ni-NTA (Quigan, Germantown, Md.) column (15-50 mL) was used for separation. Two buffers were prepared, 1) a lysis/nickel equilibration and wash buffer and 2) a nickel elution buffer. The lysis/equilibration/wash buffer was prepared as such: 25 mM HEPES buffer at pH 7.5, 250 mM NaCl, 20 mM imidazole, and 14 mM 3-mercaptoethanol as final concentrations. The elution buffer was prepared as such: 25 mM HEPES at pH 7.5, 250 mM NaCl, 400 mM imidazole, and 14 mM β-mercaptoethanol as final concentrations. The buffers were each filtered with a 0.22 μm filter prior to use. The cell pellet (1 L culture) was resuspended in 300 mL of the lysis/equilibration buffer. The cells were then lysed (3 times) with a Microfluidics Model 110Y microfluidizer (Microfluidics Corporation, Newton, Mass.). The slurry was centrifuged with a Beckman Coulter Model LE-80K ultracentrifuge (Beckman Coulter, Fullerton, Calif.) at 40,000 rpm for 45 minutes at 4° C. The supernatant was transferred to a chilled flask. A volume of 20 μl was saved for gel analysis. A Pharmacia AKTA (GMI, Inc., Ramsey, Minn.) purification system was used for separation. The prime lines were purged with lysis/equilibration buffer. The Ni-NTA column was equilibrated with 200 mL of the lysis/equilibration buffer at a flow rate of 5 mL/minute. The supernatant was loaded over the column at 4 mL/minute and the flow-through was collected in a flask. The unbound proteins were washed with lysis/equilibration buffer at a flow rate of 5 mL/minute until the ultraviolet reaches baseline. The protein was then eluted from the column with the imidazole elution buffer via imidazole gradient 20 mM to 400 mM over 320 mL. The column was then stripped of any additional protein with 80 mL of the elution buffer. The elution fractions were each 8 mL, for a total yield of 50 samples. Fractions were analyzed by sodium dodecyl sulfate polyacrylamide (SDS-PAGE) and the fractions containing protein of interest were pooled and concentrated to 10 mL using ultrafiltration cell with a 10,000 molecular weight cut-off (MWCO) Millipore membrane (Sigma-Aldrich, St. Louis, Mo.) under nitrogen gas (60 psi). Protein was further purified by size exclusion chromatography (SEC) using a Sedex 75 evaporative light scattering detector (320 mL) (Amersham Pharmacia, Uppsala, Sweden). SEC was equilibrated with 450 mL sizing buffer containing 25 mM HEPES pH 7.0, 50 mM NaCl, and 5 mM dithiothreitol. Concentrated protein was then loaded over SEC and elution with 400 mL sizing buffer was performed overnight at 0.5 mL/minute. The elution fractions were 5 mL each. The fractions were analyzed by SDS-PAGE and protein containing fractions were pooled. Concentration was measured using Bradford Assay/BSA Standard. Purified protein was stored in small aliquots at −80° C.

Assay 1: Evaluating Activator Potency and Maximum Activation at 5 mM Glucose

Full-length glucokinase (beta cell isoform) was His-tagged at the N-terminus and purified by a Ni column followed by size exclusion chromatography as described above. Glucose was obtained from Calbiochem (San Diego, Calif.) and other reagents were purchased from Sigma-Aldrich (St. Louis, Mo.).

All assays were performed in a Corning 384-well plate using Spectramax PLUS spectrophotometer (Molecular Devices, Sunnyvale, Calif.) at room temperature. The final assay volume was 40 μL. The buffer conditions used in this assay were as follows: 50 mM HEPES, 5 mM glucose, 2.5 mM ATP, 3.5 mM $MgCl_2$, 0.7 mM NADH, 2 mM dithiothreitol, 1 unit/mL pyruvate kinase/lactate dehydrogenase (PK/LDH), 0.2 mM phosphoenolpyruvate, and 25 mM KCl. The buffer pH was 7.1. The test compound in dimethylsulfoxide solution was added to the buffer and mixed by a plate shaker for 7.5 minutes. The final concentration of dimethylsulfoxide introduced into the assay was 0.25%.

Glucokinase was added to the buffer mixture to initiate the reaction in the presence and absence of compound. The reaction was monitored by absorbance at 340 nm due to the depletion of NADH. The initial reaction velocity was measured by the slope of a linear time course of 0-300 seconds. The percentage of maximum activation was calculated by the following equation:

% Maximum Activation=$(Va/Vo-1) \times 100$;

wherein each of Va and Vo is defined as the initial reaction velocity in the presence and absence of the tested compound, respectively.

To determine the $EC_{50}$ (half maximal effective concentration) and % maximum activation, compounds were serially diluted in dimethylsulfoxide by 3-fold. The glucokinase activities were measured as a function of compound concentrations. The data were fitted to the equation below to obtain the $EC_{50}$ and % max activation values:

$Va/Vo = 1+$(% max activation/100)/(1+$EC_{50}$/compound concentration).

The $EC_{50}$ (μM) and percent maximum activation data for Examples 1-4 obtained from the biological Assay 1 as defined above are presented in Table 1.

TABLE 1

$EC_{50}$ of representative examples determined by the method of Assay 1.

| Example | $EC_{50}$ (μM) at 5 mM glucose | Maximum Activation (%) at 5 mM glucose | N |
|---|---|---|---|
| 1 | 64 | 100 | 1 |
| 2 | 0.453 | 117 | 1 |
| 3 | 5.6-7.1 | 139-143 | 2 |
| 4 | 0.27-0.37 | 99-100 | 2 |

Assay 2: Evaluating Activator Potency in a Matrix Assay at Multiple Glucose Concentrations As described by Bebernitz and coworkers (Bebernitz, G. R. et. al., J. Med. Chem. 2009, 52, 6142-6152) the potency of a glucokinase activator and its modulation of the glucokinase enzyme's Km (for glucose) and Vmax can be characterized using a matrix assay wherein multiple combinations of activator and glucose concentrations are simultaneously evaluated. Utilizing an adaptation of this method, representative compounds of the current invention were evaluated at 22 different concentrations and 16 different glucose concentrations in a coupled enzyme assay system that detects glucokinase activity via depletion of β-NADH. The readout is absorbance at 340 nm, and is captured as ΔA340/Δtime.

Initially, a 1.0 L volume of assay buffer (at 5 times (5×) final concentration) was prepared utilizing the following reagents (reagent used, formula weight of reagent, 5× concentration of reagent ([5×]), final concentration of reagent after dilution ([Final], and mass of reagent):

HEPES, FW=238.3 g/mol, [5×]=250 mM, [Final]=50 mM, 59.58 g; $MgCl_2$, FW=203.3 g/mol, [5×]=17.5 mM, [Final]=3.5 mM, 3.56 g; KCl, FW=74.55 g/mol, [5×]=125 mM, [Final]=25 mM, 9.32 g; and BSA, n/a, [5×]=0.5%; [Final]=0.1%.

Compounds are tested against 16 concentrations of glucose. The glucose titration is made at 2 times (2×) the final concentration. The final glucose concentrations used are: 0 mM, 0.05 mM, 0.1 mM, 0.3 mM, 0.625 mM, 1.25 mM, 2.5 mM, 5 mM, 7.5 mm, 10 mM, 15 mM, 20 mM, 40 mM, 60 mM, 80 mM and 100 mm. Plates are stored at 4° C. The glucokinase activator compounds of Formula (I) of the current invention are evaluated at 22 different compound concentrations. The final compound concentrations that are employed are: 0.001 M, 0.0005 M, 0.00025 M, 0.000125 M, 0.0000625 M, 0.00003125 M, 0.000015625 M, $7.81 \times 10^{-6}$ M, $3.91 \times 10^{-6}$ M, $1.95 \times 10^{-6}$ M, $9.77 \times 10^{-7}$ M, $4.88 \times 10^{-7}$ M, $2.44 \times 10^{-7}$ M, $1.22 \times 10^{-7}$ M, $6.10 \times 10^{-8}$ M, $3.05 \times 10^{-8}$ M, $1.53 \times 10^{-8}$ M, $7.63 \times 10^{-6}$ M, $3.81 \times 10^{-6}$ M, $1.91 \times 10^{-6}$ M, $9.54 \times 10^{-10}$ M and $4.77 \times 10^{-10}$ M.

The assay reagents and final concentrations of the reagents are as follows (reagent, final concentration): GK, 10 nM; Buffer, 1×; dd$H_2O$; DTT, 2 mM; PEP, 0.8 mM; NADH, 0.7 mM; ATP, 2.5 mM; and PK/LDH, 8 U/mL. The DTT is stored as a frozen 1 M stock. PEP, NADH, and ATP are weighed out as powders. The assay reagents are made up fresh daily, and in two separate components.

The enzyme mix and the substrate mix is outlined as follows. The enzyme mix consists of GK, Buffer (5×), water and DTT. The substrate mix consists of Buffer (5×), water, DTT, PEP, NADH, ATP and PK/LDH. Each mix is made up at 4 times the concentration of the final concentration used.

Assay Protocol: The assay volume is 40 μL per well: 20 μL from glucose, 10 μL from enzyme, and 10 μL from substrate. The final assay plates have 1 μL of compound solution or control in DMSO. When running multiple plates simultaneously on multiple readers, read triplicates on the same reader to decrease variability.

The procedure for carrying out the assay is as follows: Add 20 μL of glucose to each well and centrifuge (1000 rpm, 10 seconds). Add 10 μL of the enzyme mix. Shake plates on plate shaker (900 revolutions per minute) at room temperature (22° C.) for 7 minutes to mix in the compound. Add 10 μl of substrate mix. Shake briefly at room temperature to mix, about 10 seconds and centrifuge to remove bubbles. Examine plate for residual bubbles, and remove them with ethanol vapor. The assay plates are read on a SpectraMax reader (Molecular Devices) using SoftMaxPro 4.8 software. The reader should be configured to read absorbance at wavelength 340 nm, in kinetic mode, read every 30 seconds for 10 minutes. Automix and blanking are off and autocalibrate is set to once.

These data were analyzed by fitting curves to the rates observed for each combination of substrate and activator. This enabled determination of the glucokinase Km (for glucose) and Vmax of at each concentration of activator. Plotting the resulting Km values for each concentration of activator and fitting a curve enabled determination of an intrinsic potency for a given activator determined as the concentration of compound affording a 50% reduction in the enzyme's Km. These intrinsic EC50 values are reported for representative compounds in Table 2.

TABLE 2

$EC_{50}$ of representative examples determined by the method of Assay 2.

| Example | Intrinsic $EC_{50}$ (μM) | N |
|---------|--------------------------|---|
| 5 | 0.22-0.31 | 3 |
| 6 | 8.9 | 1 |
| 7 | 3.3 | 1 |
| 8 | 2.3 | 1 |
| 9 | 1.25 | 1 |

We claim:

1. A compound of Formula (I)

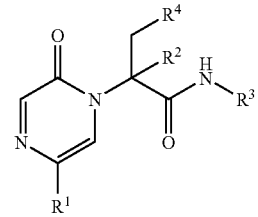

(I)

wherein:

$R^1$ is H, ($C_1$-$C_3$)alkyl, or halo-substituted ($C_1$-$C_3$)alkyl;

$R^2$ is H or ($C_1$-$C_3$)alkyl;

$R^3$ is 5- or 6-membered heteroaryl containing one or two nitrogen heteroatoms, where said heteroaryl is optionally substituted with $R^{3a}$, where $R^{3a}$ is ($C_1$-$C_3$)alkyl, —$CF_3$, cyano, ($C_1$-$C_3$)alkoxy, halo, amino, ($C_1$-$C_3$)alkylamino-, di-($C_1$-$C_3$)alkylamino-, —C(O)$OR^{3b}$, —($C_1$-$C_3$)alkylC(O)$OR^{3b}$, —C(O)$NR^{3b}R^{3c}$, or aryl($C_1$-$C_3$)alkyl-, where $R^{3b}$ and $R^{3c}$ are each independently H or ($C_1$-$C_3$)alkyl, and where the aryl of said aryl($C_1$-$C_3$)alkyl is optionally substituted with ($C_1$-$C_3$)alkyl, —$CF_3$, cyano, ($C_1$-$C_3$)alkoxy, or halo;

$R^4$ is ($C_1$-$C_6$)alkyl or

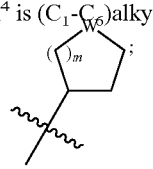

W is —$CH_2$ or O; and m is 0, 1 or 2; or a pharmaceutically acceptable salt thereof.

2. The compound of claim 1 wherein: $R^1$ is H, methyl, ethyl, —$CH_2F$, —$CHF_2$, or —$CF_3$; and $R^2$ is H, methyl, or ethyl; or a pharmaceutically acceptable salt thereof.

3. The compound of claim 2 wherein: $R^1$ is H, methyl, ethyl, —$CHF_2$, or —$CF_3$; $R^2$ is H or methyl; and $R^3$ is pyrazolyl, pyridinyl, pyridazinyl, pyrimidinyl, or pyrazinyl, each optionally substituted with $R^{3a}$, where $R^{3a}$ is ($C_1$-$C_3$)alkyl, —$CF_3$, cyano, ($C_1$-$C_3$)alkoxy, halo, amino, ($C_1$-$C_3$)alkylamino-, di-($C_1$-$C_3$)alkylamino-, —C(O)$OR^{3b}$, —($C_1$-$C_3$)alkylC(O)$OR^{3b}$, —C(O)$NR^{3b}R^{3c}$, or aryl($C_1$-$C_3$)alkyl-, where $R^{3b}$ and $R^{3c}$ are each independently H or $(C_1-C_3)$alkyl, and where the aryl of said arylalkyl is optionally substituted with $(C_1-C_3)$alkyl, —$CF_3$, cyano, $(C_1-C_3)$alkoxy, or halo; or a pharmaceutically acceptable salt thereof.

4. The compound of claim 3 wherein: $R^1$ is —$CHF_2$ or —$CF_3$; $R^3$ is a group of Formula (a), a group of Formula (b), or a group of Formula (c),

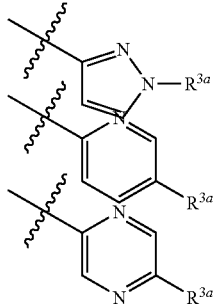

where $R^{3a}$ is methyl, ethyl, cyano, methoxy, ethoxy, F, Cl, amino, —$NHCH_3$, —$NHCH_2CH_3$, —$N(CH_3)_2$, —$CO_2H$, —$CH_2CO_2H$, —$C(O)NHCH_3$, —$C(O)N(CH_3)_2$, or benzyl, where said benzyl is optionally substituted with methyl, ethyl, methoxy, or ethoxy; or a pharmaceutically acceptable salt thereof.

5. The compound of claim 1 of the Formula (1E)

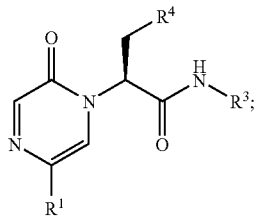

or a pharmaceutically acceptable salt thereof.

6. The compound of claim 5 wherein $R^1$ is trifluoromethyl; or a pharmaceutically acceptable salt thereof.

7. The compound of claim 5 wherein $R^3$ is pyridinyl or pyrazinyl, each optionally substituted with a methyl, —$CO_2H$ or —$H_2CO_2H$; or a pharmaceutically acceptable salt thereof.

8. The compound of claim 5 wherein $R^4$ is isopropyl, cyclobutyl, cyclopentyl, cyclohexyl or tetrahydropyranyl; or a pharmaceutically acceptable salt thereof.

9. The compound of claim 5 wherein $R^1$ is trifluoromethyl; $R^3$ is pyridinyl or pyrazinyl, each optionally substituted with a methyl, —$CO_2H$ or —$CH_2CO_2H$ and $R^4$ is isopropyl, cyclobutyl, cyclopentyl, cyclohexyl or tetrahydropyranyl; or a pharmaceutically acceptable salt thereof.

10. The compound of claim 9 wherein $R^3$ is pyrazin-2-yl, 5-methylpyridin-2-yl, 5 carboxylpyridin-2-yl or 5-(carboxymethyl)pyridin 2-yl; or a pharmaceutically acceptable salt thereof.

11. The compound of claim 10 selected from the group consisting of:
   (S)-N-(5-methylpyridin-2-yl)-2-(2-oxo-5-(trifluoromethyl)pyrazin-1(2H)-yl)-3-(tetrahydro-2H-pyran-4-yl)propanamide;
   (S)-6-(3-cyclopentyl-2-(2-oxo-5-(trifluoromethyl)pyrazin-1(2H)-yl)propanamido)nicotinic acid;
   (S)-3-cyclopentyl-2-(2-oxo-5-(trifluoronnethyl)pyrazin-1(2H)-yl)-N-(pyrazin-2-yl)propanamide;
   (S)-3-cyclopentyl-N-(5-methylpyridin-2-yl)-2-(2-oxo-5-(trifluoromethyl)pyrazin-1(2H)-yl)propanamide;
   (S)-6-(3-cyclohexyl-2-(2-oxo-5-(trifluoromethy)pyrazin-1(2H)-yl)propananmido)nicotinic acid;
   (S)-6-(2-(2-oxo-5-(trifluoromethyl)pyrazin-1(2H)-yl)-3-(tetrahydro-2H-pyran-4-yl)propanamido)nicotinic acid;
   (S)-6-(4-methyl-2-(2-oxo-5-(trifluoronnethyl)pyrazin-1(2H)-yl)pentanamido)nicotinic acid;
   (S)-2-(6-(3-cyclopentyl-2-(2-oxo-5-(trifluoromethyl)pyrazin-1(2H)-yl)propanamido)pyridin-3-yl)acetic acid; and
   (S)-6-(3-cyclobutyl-2-(2-oxo-5-(trifluoromethyl)pyrazin-1(2H)-yl)propanamido)nicotinic acid; or a pharmaceutically acceptable salt thereof.

12. A pharmaceutical composition comprising a therapeutically effective amount of a compound of any one of claims 1 to 11, or a pharmaceutically acceptable salt thereof, and a pharmaceutically acceptable excipient, diluent, or carrier.

* * * * *